US008937154B2

(12) United States Patent
Debnath et al.

(10) Patent No.: US 8,937,154 B2
(45) Date of Patent: Jan. 20, 2015

(54) STABILIZED THERAPEUTIC SMALL HELICAL ANTIVIRAL PEPTIDES

(75) Inventors: Asim Kumar Debnath, Fort Lee, NJ (US); Hongtao Zhang, Mount Vernon, NY (US); Qian Zhao, Rego Park, NY (US)

(73) Assignee: New York Blood Center, Inc., New York, NY (US)

( * ) Notice: Subject to any disclaimer, the term of this patent is extended or adjusted under 35 U.S.C. 154(b) by 150 days.

(21) Appl. No.: 13/364,667

(22) Filed: Feb. 2, 2012

(65) Prior Publication Data

US 2012/0165249 A1 Jun. 28, 2012

Related U.S. Application Data

(63) Continuation-in-part of application No. 12/438,414, filed as application No. PCT/US2007/021156 on Oct. 2, 2007.

(60) Provisional application No. 60/849,551, filed on Oct. 5, 2006, provisional application No. 61/497,460, filed on Jun. 15, 2011.

(51) Int. Cl.

| | |
|---|---|
| ***C07K 7/06*** | (2006.01) |
| ***A61K 38/00*** | (2006.01) |
| ***A61K 38/04*** | (2006.01) |
| ***C07K 7/00*** | (2006.01) |

(52) U.S. Cl.

CPC .. *C07K 7/06* (2013.01); *A61K 38/00* (2013.01)

USPC ............. 530/326; 530/327; 530/328; 514/1.1

(58) Field of Classification Search

None

See application file for complete search history.

(56) References Cited

U.S. PATENT DOCUMENTS

| | | | | |
|---|---|---|---|---|
| 6,187,548 | B1 | 2/2001 | Akerstrom et al. | |
| 6,239,270 | B1 | 5/2001 | Akerstrom et al. | |
| 6,653,102 | B2 | 11/2003 | Roch et al. | |
| 6,790,950 | B2 | 9/2004 | Lowery et al. | |
| 7,723,469 | B2 | 5/2010 | Walensky et al. | |
| 7,763,262 | B2 | 7/2010 | Lowery et al. | |
| 7,820,786 | B2 | 10/2010 | Thomson | |
| 8,324,153 | B2 | 12/2012 | Debnath | |
| 2005/0250680 | A1 | 11/2005 | Walensky et al. | |
| 2006/0008848 | A1 | 1/2006 | Verdine et al. | |
| 2009/0149630 | A1 | 6/2009 | Walensky et al. | |
| 2009/0176964 | A1 | 7/2009 | Walensky et al. | |
| 2010/0130430 | A1* | 5/2010 | Debnath et al. | 514/13 |
| 2010/0151483 | A1 | 6/2010 | Hornbeck et al. | |
| 2010/0159477 | A1 | 6/2010 | Hornbeck et al. | |
| 2010/0168388 | A1 | 7/2010 | Bernal et al. | |
| 2010/0267608 | A1 | 10/2010 | Das Gupta et al. | |
| 2010/0286057 | A1 | 11/2010 | Walensky et al. | |
| 2011/0218155 | A1 | 9/2011 | Walensky et al. | |
| 2011/0318352 | A1 | 12/2011 | Walensky | |
| 2012/0165249 | A1* | 6/2012 | Debnath et al. | 514/3.8 |
| 2013/0059776 | A1 | 3/2013 | Debnath | |

FOREIGN PATENT DOCUMENTS

| | | | |
|---|---|---|---|
| WO | 98/40744 | A1 | 9/1998 |
| WO | 00/61724 | A2 | 10/2000 |
| WO | 2005/044839 | A2 | 5/2005 |
| WO | 2008/045238 | A2 | 4/2008 |

OTHER PUBLICATIONS http://en.wikipedia.org/wiki/Capsid (Last Updated: Jul. 25, 2014).*

Bhattacharya Shibani et al., "Solution structure of a hydrocarbon stapled peptide inhibitor in complex with monomeric C-terminal domain of HIV-1 capsid", Journal of Biological Chemistry, vol. 283(24), Jun. 2008, pp. 16274-16278.

Debnath et al. "Structure-Based Identification of Small Molecul Antiviral Compounds Targeted to the gp41 Core Structure of the Human Immunodeficiency Virus Type 1." J. Med. Chem. 1999, 42, 3203-3209.

Del Alamo et al. "Thermodynamic Dissection of a Low Affinity Protein0Protein Interface Involved in Human Immunodeficiency Virus Assembly." The Journal of Biological Chemistry, vol. 278, No. 30, pp. 27923-27929, 2003.

Ehrlich et al. "HIV-1 Capsid Protein Forms Spherical (Immature-Like) and Tubular (Mature-Like) Particles in Vitro: Structure Switching by pH-induced Conformational Changes." Biophysical Journal, vol. 81, 586-594, 2001.

Gross et al. "In vitro assembly propertied of purified bacterially expressed capsid proteins of human immunodeficiency virus." Eur. J. Biochem. 249, 592-600, 1997.

Jiang et al. "A screening assay for antiviral compounds targeted to the HIV-1 gp41 core structure using a conformation-specific monoclonal antibody." Journal of Virological Methods 80, 1999, 85-96.

Jiang et al. "Development of HIV Entry Inhibitors Targeted to the Coiled-Coil Regions of gp41." Biochemical and Biophysical Research Communications 269, 641-646, 2000.

Lalezari et al. "Enfuvirtide, an HIV-1 Fusion Inhibitor, for Drug-Resistant HIV Infection in North and South America." The New England Journal of Medicine, 2003, vol. 348, No. 22.

Liu et al. "Theaflavin derivatives in black tea and catechin derivatives in green tea inhibit HIV-1 entry by targeting gp41." Biochimica et Biophysica Acta 1723, 2005, 270-281.

Naicker et al. "Synthesis and anti-HIV-1 activity of 4-[4-(4,6-bisphenylamino-[1,3,5]triazin-2-ylamino)-5-methoxy-2-methylphenylazo]-5-hydroxynaphthalene-2<7-disulfonic acid and its derivatives." Bioorganic & Medicinal Chemistry 12, 2004, 1215-1220.

Neurath et al. "Blocking of CD4 Cell Receptors for the Human Immunodeficiency Virus Type 1 (HIV-1) by Chemically Modified Bovine Milk Proteins: Potential for AIDS Prophylaxis." Journal of Molecular Recognition, vol. 8, 304-316, 1995.

(Continued)

*Primary Examiner* — Maury Audet

(74) *Attorney, Agent, or Firm* — K&L Gates LLP; Louis C. Cullman; Michelle Glasky Bergman

(57) ABSTRACT

Provided are constrained peptides that inhibit HIV assembly. Pharmaceutical compositions comprising the above peptides are also provided. Additionally provided are methods of inhibiting replication of a capsid-containing virus.

12 Claims, 14 Drawing Sheets

(56) References Cited

OTHER PUBLICATIONS

Neurath et al. "Structural Requirements for and Consequences of an Antiviral Porphyrin Binding to the V3 Loop of the Human Immunodeficiency Virus (HIV-1) Envelope of Glycoprotein gp120." Journal of Molecular Recognition, vol. 8, 345-357, 1995.
Neurath et al. "Cellulose acetate phthalate, a common pharmaceutical excipient, inactivates HIV-1 and blocks the coreceptor binding site on the virus envelope glycoprotein gp120." BMC Infectious Diseases 2001, 1:17.
Neurath et al. "Anti-HIV-1 activity of cellulose acetate phthalate: Synergy with soluble CD4 and induction of "dead end" gp41 six helix bundles." BMC Infectious Diseases 2002, 2:6.
Zhang et al. "A Cell-penetrating Helical Peptide as a Potential HIV-1 Inhibitor." J. Mol. Biol. 2008; 378(3) 565-580.
Zhao et al. "XTT Formazan Widely Used to Detect Cell Viability Inhibits HIV Type 1 Infection in Vitro by Targeting gp41." AIDS Research and Human Retroviruses, vol. 18, No. 14, 2002, pp. 989-997.
Zhao et al. "A novel assay to identify entry inhibitors that block binding of HIV-1 gp120 to CCR5."Virology 326, 2004, 299-309.
Abdurahman, S., Hoglund, S., Goobar-Larsson, L., & Vahlne, A. Selected ammo acid substitutions in the C-terminal region of human immunodeficiency virus type 1 capsid protein affect virus assembly and release. J Gen Virol 85, 2903-2913 (2004).
Chien, A.I., Liao, W.H., Yang, D.M., & Wang, CT. A domain directly C-terminal to the major homology region of human immunodeficiency type 1 capsid protein plays a crucial role in directing both virus assembly and incorporation of Gag-Pol. Virology. 348, 84-95 (2006).
Chu, H.H., Chang, Y.F., & Wang, CT. Mutations in the alpha-helix Directly C-terminal to the Major Homology Region of Human Immunodeficiency Virus Type 1 Capsid Protein Disrupt Gag Multimerization and Markedly Impair Virus Particle Production. J Biomed. Sci. 13, 645-56 (2006).
Derdeyn, CA. et al. J Virol. 74, 8358 (2000).
Derdowski, A., Ding, L., & Spearman, P. A Novel Pluorescence Resonance Energy Transfer Assay Demonstrates that the Human Immunodeficiency Virus Type 1 Pr55Gag I Domain Mediates Gag-Gag Interactions. The Journal of Virology 78, 1230-1242 (2004).
Dong, X. et al. AP-3 directs the intracellular trafficking of HIV-I Gag and plays a key role in particle assembly. Cell. 120, 663-674 (2005).
Douglas, CC, Thomas, D., Lanman, J., & Prevelige, P.E., Jr. Investigation of N- terminal domain charged residues on the assembly and stability of HIV-I CA. Biochemistry.43, 10435-10441 (2004).
Forshey, B.M., von Schwedler, U., Sundquist, W.I., & Aiken, C Formation of a human immunodeficiency virus type 1 core of optimal stability is crucial for viral replication. J Virol. 76, 5667-5677 (2002).
Freed, E.O. HIV-I gag proteins: diverse functions in the virus life cycle. Virology. 251, 1-15 (1998).
Garzon, M.T. et al. The dimerization domain of the HIV-I capsid protein binds a capsid protein-derived peptide: a biophysical characterization. Protein Sci 13, 1512-1523 (2004).
Ganser-Pornillos, B.K., von Schwedler, U.K., Stray, K.M., Aiken, C, & Sundquist, W.I. Assembly properties of the human immunodeficiency virus type 1 CA protein. J Virol 78, 2545-2552 (2004).
Gottlinger, H.G. The HIV-I assembly machine. AIDS Suppl 5, S13-S20 (2001).
Grigorov, B., Arcanger, F., Roingeard, P., Darlix, J.L., & Muriaux, D. Assembly of infectious HPV-I in human epithelial and T-lymphoblastic cell lines. J Mol Biol. 359, 848-862 (2006).
Gross, I. et al. J. Virol 72, 4798 (1998).
Guo, X. et al. The R362A mutation at the C-terminus of CA inhibits packaging of human immunodeficiency virus type 1 RNA. Virology 343, 190-200 (2005).
Hoglund, S. et al. Tripeptide interference with human immunodeficiency virus type 1 morphogenesis. Antimicrob. Agents Chemother. 46, 3597-3605 (2002).
Huseby, D., Barklis, R.L., Alfadhli, A., & Barklis, E. Assembly of human immunodeficiency virus precursor gag proteins. J Biol. Chem. 280, 17664-17670 (2005).
Jiang, S., et al. Journal of Experimental Medicine 174, 1557-1563 (1991).
Jiang, S. et al. Antimicrobial Agents and Chemotherapy 48, 4349-4359 (2004).
Joshi, A., Nagashima, K., & Freed, E.O. Mutation of dileucine-like motifs in the human immunodeficiency virus type 1 capsid disrupts virus assembly, gag-gag interactions, gag- membrane binding, and virion maturation. J Virol. 80, 7939-7951 (2006).
Kieber-Emmons et al. Curr. Opin. Biotechnol. 8, 435-441 (1997).
Kramer, B. et al. HIV interaction with endosomes in macrophages and dendritic cells. Blood Cells Mol Dis. 35, 136-142 (2005).
Leduc, A.M. et al. Helix-stabilized cyclic peptides as selective inhibitors of steroid receptor-coactivator interactions. Proc Natl Acad Sci U S A. 100, 11273-11278 (2003).
Li, F. et al. PA-457: a potent HIV inhibitor that disrupts core condensation by targeting a late step in Gag processing. Proc Natl Acad Sci U S A 100, 13555-13560 (2003).
Morikawa, Y. HIV capsid assembly. Curr HIV Res 1, 1-14 (2003).
Lundberg, M. et al. Biochem. Biophys. Res. Commun., 291, 367 (2002).
Niedrig, M. et al. Inhibition of infectious human immunodeficiency virus type 1 particle formation by Gag protein-derived peptides. J Gen Virol 75 ( Pt 6), 1469-1474 (1994).
Nydegger, S., Foti, M., Derdowski, A., Spearman, P., & Thali, M. HIV-I egress is gated through late endosomal membranes. Traffic. 4, 902-910 (2003).
Ono, A. & Freed, E.O. Cell-type-dependent targeting of human immunodeficiency virus type 1 assembly to the plasma membrane and the multivesicular body. J Virol. 78, 1552-1563 (2004).
Pelchen-Matthews, A., Kramer, B., & Marsh, M. Infectious HIV-I assembles in late endosomes in primary macrophages. J. Cell Biol. 162, 443-455 (2003).
Phelan, J.C., Skelton, N.J., Braisted, A.C., & McDowell, R.S. A General Method for Constraining Short Peptides to an a-Helical Conformation. J. Am. Chem. Soc. 119, 455-460 (1997).
Qiu, W. et al. Tetrahedron, 56, 2577 (2000).
Richard, JP et al. J. Biol. Chem., 278, 585 (2003).
Ripka et al. Curr. Opin. Chem. Biol. 2, 441-452 (1998).
Sakalian, M. et al. 3-O-(3',3'-dimethysuccinyl) betulinic acid inhibits maturation of the human immunodeficiency virus type 1 Gag precursor assembled in vitro. J Virol 80:5716-5722 (2006).
Sanderson. Med. Res. Rev. 19, 179-197 (1999).
Schafrneister, C.E., Po ,J., & Verdine, G.L. An All-Hydrocarbon Cross-Linking System for Enhancing the Helicity and Metabolic Stability of Peptides. J. Am. Chem. Soc. 122, 5891-5892 (2000).
Sherer, N.M. et al. Visualization of retroviral replication in living cells reveals budding into multivesicular bodies. Traffic. 4, 785-801 (2003).
Tang, C. et al. Antiviral inhibition of the HTV-I capsid protein. J Mol Biol. 327, 1013-1020 (2003).
Wang, D., Liao, W., & Arora, P.S. Enhanced Metabolic Stability and Protein-Binding Properties of Artificial Helices Derived from a Hydrogen-Bond Surrogate: Application to Bc1-xL. Angewandte Chemie International Edition 44, 6525-6529 (2005).
Walensky, L.D. et al. Activation of Apoptosis in Vivo by a Hydrocarbon-Stapled BH3 Helix. Science 305, 1466-1470 (2004).
Yang, B., Liu, D., & Huang, Z. Synthesis and helical structure of lactam bridged BH3 peptides derived from pro-apoptotic Bcl-2 family proteins. Bioorganic & Medicinal Chemistry Letters 14, 1403-1406 (2004).
Sticht et al. "A peptide inhibitor of HIV-1 assembly in vitro", Nature Structural & Molecular Biology, 12:671-677, 2005.
Ternois et al., "The HIV-1 capsid protein C-terminal domain in complex with a virus assembly inhibitor", Nature Structural & Molecular Biology, Aug. 2005, vol. 12, No. 8, pp. 678-682.
Shoelson et al. "YNXM motifs of IRS-1 define substrate specificity of the insulin receptor kinase." PNAS USA 89:2027-2031, 1992.

* cited by examiner

Ile-Thr-Phe-X-Asp-Leu-Leu-X-Tyr-Tyr-Gly-Lys-Lys-Lys-NH2

X = (S)-2-(4'-pentenyl)Ala

NYAD-13 SEQ ID NO:7

Ile-Thr-Phe-Glu-Asp-Leu-Leu-X-Tyr-Tyr-Gly-X-Lys-Lys-NH2

X = (S)-2-(4'-pentenyl)Ala

NYAD-14 SEQ ID NO:9

Ile-Ser-Phe-Z-Glu-Leu-Leu-Asp-Tyr-Tyr-X-Glu-Ser-Gly-Ser-NH2

X = (S)-2-(4'-pentenyl)Ala
Z = (S)-2-(7'-octanyl)Ala

NYAD-36 SEQ ID NO:8

Ala-Gln-Ala-Val-Lys-X-Trp-Met-Thr-X-Thr-Leu-Leu-Val-Ala-Lys-Lys-Lys-NH2

X = (S)-2-(4'-pentenyl)Ala

NYAD-203 SEQ ID NO:10

NYAD-15 I-S-F-X-E-L-L-X-Y-Y-G-R SEQ ID NO:11

NYAD-23 I-T-F-X-D-I-L-X-Y-Y-G-E-K SEQ ID NO:12

NYAD-24 I-S-F-X-E-L-L-X-Y-Y-G-E-K SEQ ID NO:13

NYAD-31 I-T-F-X-D-W-L-X-Y-Y-G-R SEQ ID NO:14

NYAD-33 I-S-F-Z-E-W-L-Q-Y-Y-X-R SEQ ID NO:15

NYAD-34 I-S-F-X-E-L-L-X-Y-Y-G-R-S-G-S SEQ ID NO:16

NYAD-35 I-S-F-X-E-L-L-X-Y-Y-G-E-S-G-S SEQ ID NO:17

NYAD-37 I-S-F-X-E-I-L-X-Y-Y-G-E-S-G-S SEQ ID NO:18

STABILIZED THERAPEUTIC SMALL HELICAL ANTIVIRAL PEPTIDES

CROSS REFERENCE TO RELATED APPLICATIONS

The present application is a continuation-in-part of U.S. patent application Ser. No. 12/438,414 filed Feb. 23, 2009 which is an application under section 371 of International Patent Application No. PCT/US2007/021156 filed Oct. 2, 2007 which in turn claims the benefit under 35 U.S.C. §119(e) to U.S. Provisional Application 60/849,551 filed Oct. 5, 2006. The present application also claims the benefit under 35 U.S.C. §119(e) to U.S. Provisional Application 61/497,460 filed Jun. 15, 2011. Each of these applications is incorporated herein in their entirety.

FIELD

The present disclosure generally relates to treatments for HIV infection. More specifically, the disclosure provides peptides that inhibit assembly of capsid-containing viruses and methods for using those peptides to treat capsid-containing viruses including HIV.

BACKGROUND

Assembly is a critical step in the HIV-1 life cycle and generally thought to occur through the controlled polymerization of the gag polyprotein, which is transported to the plasma membrane where the assembly takes place and the virus particles are formed and bud out as spherical immature noninfectious particles. Recent data indicate that gag polyprotein can also accumulate and assemble into viral particles in the late endosomes, often called multivesicular bodies (MVB), especially in macrophages. The virus particles are released when MVB fuses with the plasma membrane.

It has recently been shown that a cellular protein, AP-3, directs the intracellular trafficking of gag to the MVB. Immediately after the budding, the particles undergo a process termed as maturation, which is essential for the virus to become infectious, where the gag polyprotein is sequentially cleaved by the viral protease to matrix (MA), capsid (CA), nucleocapsid (NC) and p6 domains as well as two spacer proteins, SP1 and SP2. This process triggers a dramatic change in morphology of the particles and an electron dense core is formed surrounded by conical capsid. The formation of mature capsid (CA) play critical role in viral infectivity. Mutations in the CA have been shown to have detrimental effects in viral assembly. Therefore, capsid plays important role in viral assembly, which is critical in the HIV-1 life cycle and has been considered as potential target for developing new generations of drugs against HIV-1.

The major obstacle in developing drugs against assembly has been the lack of effective screening system although some new assay methods have been reported recently. Despite this difficulty, there are reports of identifying peptides or small molecule compounds that disrupt HIV-1 assembly. The first breakthrough in identifying small molecule inhibitors (CAP-1 and CAP-2) of capsid was reported by Summers' group (J Mol Biol. 327:1013-1020, 2003). Although the affinity ($K_d$) of CAP-1 to N-terminal CA (N-CA) was only ~800 μM, the identification was the initiator to search for potential inhibitors against this target. Another potent small molecule inhibitor, PA-457 which targets gag processing, has been recently reported. These small molecule inhibitors interfere with maturation of HIV-1. The later compound is currently undergoing Phase II clinical trials.

Recently, a small linear peptide (CAI) has been identified by phage display technique, which inhibits HIV-1 assembly in vitro by targeting the C-terminal CA (C-CA) of capsid. Although x-ray crystallographic analysis revealed that CAI forms a helix and binds to a hydrophobic groove formed by helices 1, 2 and 4 of C-CA, its conformation in solution has not been reported. The dissociation constant ($K_d$) was estimated to be ~15 μM. CAI was the first compound reported to have inhibition against both immature and mature HIV-1 particles in vitro. However, the major drawback of CAI is that it cannot penetrate cells, thereby, cannot be used as an assembly inhibitor in living cells.

It would be desirable to have an inhibitor of HIV assembly that can penetrate infected cells. The present disclosure addresses that need.

SUMMARY

The present disclosure is based on the discovery that α-helical peptides that are anti-viral in vitro but cannot penetrate cells, can be made to penetrate cells and be active in vivo if the peptide is stabilized using cross-linking procedures that increase the α-helicity of the peptide in solution.

In one embodiment, disclosed herein is a peptide comprising a amino acid sequence selected from the group consisting of SEQ ID NOs:7-19 wherein the alpha carbons of the unnatural amino acids X and Z comprise a methyl group and an olefinic group, wherein the two olefinic groups of the unnatural amino acids are on the same side of the α-helix and are joined to form a cross-link between the two unnatural amino acids and wherein X comprises (S)-α-2-(4'-pentenyl) alanine and Z comprises (S)-α-2-(7'-octanyl)alanine. In another embodiment, the amino acid sequence is SEQ ID NO:8.

In another embodiment, the peptide further comprises a detectable moiety, such as a fluorescent moiety or a radioactive moiety, a therapeutic compound such as an oligopeptide or an organic molecule, or an antigen such as an HIV antigen.

In another embodiment, disclosed herein is a pharmaceutical formulation comprising a peptide comprising an amino acid sequence selected from the group consisting of SEQ ID NOs:7-19 wherein the alpha carbons of the unnatural amino acids X and Z comprise a methyl group and an olefinic group, wherein the two olefinic groups of the unnatural amino acids are on the same side of the α-helix and are joined to form a cross-link between the two unnatural amino acids and wherein X comprises (S)-α-2-(4'-pentenyl)alanine and Z comprises (S)-α-2-(7'-octanyl)alanine.

In one embodiment, a method is provided for inhibiting replication of a capsid-containing virus in a cell, the method comprising contacting the cell with the peptide in a manner sufficient to inhibit replication of the capsid-containing virus in the cell. In another embodiment, the cell is in a mammal infected with the capsid-containing virus. In another embodiment, the virus is a human immunodeficiency virus. In yet another embodiment, the method further comprises treating the mammal with at least one additional anti-viral agent.

In another embodiment, a method is provided for treating a mammal infected with a capsid-containing virus, comprising administering the pharmaceutical formulation in a manner sufficient to treat the mammal. In another embodiment, the virus is a human immunodeficiency virus. In yet another embodiment, the method further comprises treating the mammal with at least one additional anti-viral agent.

In one embodiment, a peptide from 10 to 23 amino acids long is disclosed, wherein two of the amino acids are unnatural amino acids having either R or S stereochemistry at the α-carbon, wherein the α-carbon of the unnatural amino acids comprises a methyl group and an olefinic group, where the two olefinic groups of the unnatural amino acids are on the same side of the α-helix and are joined to form a cross-link between the two unnatural amino acids, wherein the sequence of the amino acids of the peptide comprises I(T/S)FE(D/E)(L/I/W)L(D/Q)YY (SEQ ID NO:21) or mimetics thereof; wherein the two unnatural amino acids replace two of the amino acids at any positions selected from the group consisting of 3 amino acids apart (i and i+3), 4 amino acids apart (i and i+4) and 7 amino acids apart (i and i+7); and wherein the cross-link between the two unnatural amino acids is a C1-C10 alkyl, alkenyl, alkynyl, $(R1\text{-}K\text{-}R1)_N$; each of which is substituted with a 0-6 R2, wherein R1 is an alkyl, alkenyl or alkynyl; K is O, S, SO, $SO_2$, CO, CONR4, or

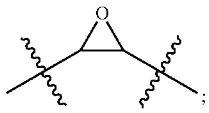 [SMILES: *C1OC1*]

;

R2 is a halo, C1-C10 alkyl, OR3, $N(R3)_2$, SR3, SOR3, $SO_2R3$, $CO_2R3$, R3, a fluorescent moiety or a radioisotope; R3 is H or a C1-C10 alkyl; R4 is H, alkyl or a therapeutic agent; and n is an integer from 1-4.

In another embodiment, the unnatural amino acids comprise (S)-α-2-(4'-pentenyl)alanine or (S)-α-2-(7'-octanyl) alanine. In additional embodiments, the peptide comprises 11 to 23 amino acids and the amino acid following YY is G; the peptide comprise 11 to 23 amino acids and the amino acid following YYG is (K/E/R); the peptide comprises 12 to 23 amino acids and the amino acid following YYG(K/E/R) is (K/S); the peptide comprises 13 to 23 amino acids and the amino acid following YYG(K/E/R)(K/S) is (K/G); and the peptide comprises 14 to 23 amino acids and the amino acid following YYG(K/E/R)(K/S)(K/G) is S. In yet another embodiment, the peptide comprises an amino acid sequence selected from the group consisting of SEQ ID NOs:7-19.

BRIEF DESCRIPTION OF THE DRAWINGS

FIGS. 3A and 3D depict FITC-conjugated NYAD-1. FIGS. 3B and 3E depict gag-mStrawberry. FIGS. 3C and 3F depict merged views demonstrated colocalization of FITC-NYAD-1 with gag-mStrawberry. All samples were living cells and obtained 24 hr post-transfection.

FIGS. 4A and 4D), 5× molar excess of CAI (FIGS. 4B and 4E), and 5× molar excess of NYAD-1 (FIGS. 4C and 4F).

FIG. 9 depicts Western Blot analysis of production of viral (p24) and cellular (p55) proteins after treatment of HIV-1-infected MT-2 cells with NYAD-1 and NYAD-15.

FIG. 10 depicts Western Blot analysis of production of viral (p24) and cellular (p55) proteins after treatment of HIV-1-infected MT-2 cells with NYAD-23 and NYAD-37.

FIG. 11 depicts Western Blot analysis of production of viral (p24) and cellular (p55) proteins after treatment of HIV-1-infected MT-2 cells with NYAD-36.

FIG. 13 depicts penetration of NYAD-41 and NYAD-36 to 293T cells by confocal microscopy.

DETAILED DESCRIPTION

Figure 1:
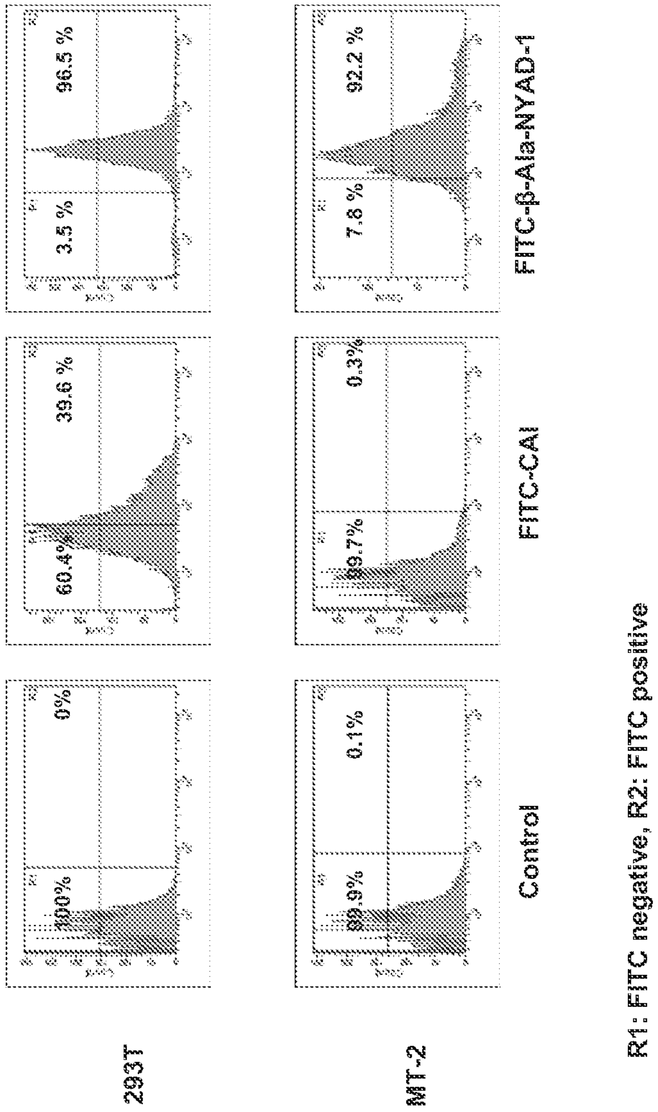
FIG. 1 depicts experimental results of cell penetration and/or association of the linear (SEQ ID NO:1; CAI) and constrained peptides (NYAD-1). The graphs are FACS analyses of 293T and MT2 cells incubated for 4 hr at 37° C. with FITC-conjugated peptides. Cells were washed 3 times with PBS before analysis. Upper panel: Left, FACS analysis of 293T cells without FITC-peptide. Center, FACS analysis of 293T cells with FITC-CAI. Right, FACS analysis of 293T cells with FITC-β-Ala-NYAD-1. Lower panel: Left, FACS analysis of MT-2 cells without FITC-peptide. Center, FACS analysis of MT-2 cells with FITC-CAI. Right, FACS analysis of MT-2 cells with FITC-β-Ala-NYAD-1.

The present disclosure is directed to peptides from 10 to 23 amino acids long, wherein two of the amino acids are unnatural amino acids having either R or S stereochemistry at the α-carbon, wherein the α-carbon of the unnatural amino acids comprises a methyl group and an olefinic group, where the two olefinic groups of the unnatural amino acids are on the same side of the α-helix and are joined to form a cross-link between the two unnatural amino acids, wherein the sequence of the amino acids of the peptide comprises (I/L/V)(T/S/A/V/C)(F/I/L/V/Y/M/W)(D/E/S)(D/E) (L/F/I/V/YM/W)(L/D/T/F/I/V/Y/M/W)(D/EA/S)(Y/F/I/L/V/M/W)(Y/F/I/L/V/M/T) (SEQ ID NO:2) or mimetics thereof, wherein the two unnatural amino acids replace two of the amino acids at any positions 3 amino acids apart (i and i+3), 4 amino acids apart (i and i+4) or 7 amino acids apart (i and i+7), and wherein the cross-link between the two unnatural amino acids is a C1-C10 alkyl, alkenyl, alkynyl, $(R1\text{-}K\text{-}R1)_n$; each of which is substituted with a 0-6 R2, wherein R1 is an alkyl, alkenyl or alkynyl; K is O, S, SO, $SO_2$, CO, CONR4, or

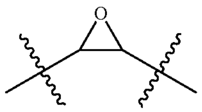 [SMILES: *C1OC1*]

R2 is a halo, C1-C10 alkyl, OR3, $N(R3)_2$, SR3, SOR3, $SO_2R3$, $CO_2R3$, R3, a fluorescent moiety or a radioisotope; R3 is H or a C1-C10 alkyl; R4 is H, alkyl or a therapeutic agent; and n is an integer from 1-4.

In the above formula, it should be understood that amino acids are only represented by letters within parentheses followed by "wherein the sequence of the amino acids of the peptide comprises", the R's outside of those parentheses (R1, R2, R3, and R4) and the K in "(R1-K-R1)" would be understood to represent variables that are subsequently defined, and the O, N, H, C, S outside of those parentheses would be understood to represent the atoms oxygen, nitrogen, hydrogen, carbon and sulfur, respectively.

It is contemplated that the peptides also encompass future variations in known procedures for stabilizing α-helices. For example, it is believed that the methyl group of the unnatural amino acids could be substituted with another small (e.g., C1-C5) alkyl, alkenyl, or alkynyl without affecting the activity of the peptide in vitro or in vivo, or the ability of the crosslink to stabilize the peptide and increase its α-helicity.

As used herein, the designation of an amino acid residue in the instant peptides as more than one amino acid (using the common one-letter amino acid code) in parenthesis with a slash between the amino acids, mean that any of the indicated amino acids, or mimetics thereof (unless specifically excluded), could occupy that residue. For example, (I/L/V)(T/S/A/V/C) means that the first residue can be any one of isoleucine, leucine, or valine, and the second residue can be any one of threonine, serine, alanine, valine, or cysteine, or mimetics.

As used herein, a mimetic or peptidomimetic is a compound that is capable of mimicking a natural parent amino acid in a protein, in that the substitution of the peptidomimetic for the natural amino acid does not affect the activity of the protein. Proteins comprising peptidomimetics are generally not substrates of proteases and are likely to be active in vivo for a longer period of time as compared to the natural proteins. In addition, they could be less antigenic and show an overall higher bioavailability. The skilled artisan would understand that design and synthesis of peptidomimetics that could substitute for amino acids of any particular peptide (such as the peptides of this disclosure) would not require undue experimentation. Nonlimiting examples of mimetics useful in this regard include D-amino acids and constrained amino acids such as norleucine, or 2-aminoisobutyric acid. It is also within the confines of the present disclosure that amino acids in the peptide sequence can be substituted with amino acids having a propensity to form alpha helices.

Each peptide can include the addition of one or more chemical groups at specific amino acid(s) and/or at the amino end and/or at carboxy end, in order to enhance the stability, reactivity and/or solubility of the peptides. For example, hydrophobic groups such as carbobenzoyl, dansyl, acetyl, a t-butyloxycarbonyl group, or a 9-fluorenylmethyoxycarbonyl group may be added to the amino terminal end of the peptide. In another example, the hydrophobic group, t-butyloxycarbonyl, or an amido group, or a para-nitrobenzyl ester group, may be added to the carboxy terminal end of the peptide. Techniques for introducing such modifications are well known to those of skill in the art.

The peptides may be in the form of any pharmaceutically acceptable salt. Acid addition salts of the compounds are prepared in a suitable solvent from the peptide and an excess of an acid, such as hydrochloric, hydrobromic, sulfuric, phosphoric, acetic, trifluoroacetic, maleic, succinic or methanesulfonic. Where the peptides include an acidic moiety, suitable pharmaceutically acceptable salts may include alkali metal salts, such as sodium or potassium salts, or alkaline earth metal salts, such as calcium or magnesium salts. A salt of the peptide in which the amino terminus is H and the carboxy terminus is $NH_2$ is preferred. Also within the scope of the present disclosure are peptides in free acid form.

The amino acid residues for the peptides disclosed herein are the combination of the specific peptide identified by Sticht et al. (2005) having the amino acid sequence ITFEDLL-DYYGP (SEQ ID NO:1; CAI), along with substitutions in that sequence that were identified by Sticht in the peptides that most frequently bound to the C-CANC protein used in that work (see Table 1 of Sticht et al., 2005). Also included are amino acids that are conservative substitutions for the Sticht et al. peptide. It is believed that peptides of any combination of the alternative amino acids or mimetics in the sequence provided would inhibit assembly of a capsid-containing virus, in vivo or in vitro (i.e., outside the cell). Such assembly inhibition can be tested without undue experimentation by, e.g., the methods described in the Examples below, or in Sticht et al., 2005.

In one embodiment, the sequence of the amino acids of the peptide comprises (I/V)(T/S)(F/W/Y)(E/S)(D/E)L(L/D/T)(D/A/S)(Y/F)(Y/M) (SEQ ID NO:3), which is the combination of the specific peptide (SEQ ID NO:1; CAI) identified by Sticht et al., along with substitutions in that sequence that were identified by Sticht et al. in the peptides that most frequently bound to the C-CANC peptide used in that work (Table 1 of Sticht et al., 2005).

It is also disclosed that the peptide comprises 11 to 23 amino acids, where the amino acid following (Y/F/I/L/V/M/T) is (G/S/T/N/H/C/L/R/D/E/Q/M/K) (SEQ ID NO:4). The amino acid options for the $11^{th}$ peptide (G/S/T/N/H/C/L/R/D/E/Q/M/K) is identified from Sticht et al., 2005, with conservative substitutions as described above. In one embodiment, the amino acid following (Y/F/I/L/V/M/T) is G.

It is it is also disclosed that the peptide comprises 12 to 23 amino acids, wherein the amino acid following (G/S/T/N/H/C/L/R/D/E/Q/M/K) is (P/M/R/K) (SEQ ID NO:5), in one embodiment P. In the certain embodiments, the sequence of the amino acids of the peptide comprises ITFEDLLDYYGP (SEQ ID NO:1).

Exemplary cross-links between the two unnatural amino acids are

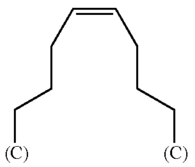

or

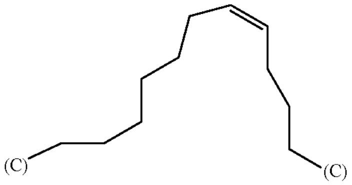

wherein the (C)s are the α-carbons of the unnatural amino acids.

In one embodiment, the unnatural amino acids are at an i and i+4 positions. In another embodiment, they replace the fourth [(D/E/S)] and the eighth [(D/E/S)] amino acids of the peptide, the seventh [(L/D/T/F/I/V/Y/M/W)] and eleventh [(G/S/T/N/H/C/L/R/D/E/Q/M)] amino acids of the peptide, or the eighth [(D/E/S)] and the twelfth [(P/M/R/K)] amino acids of the peptide.

In one embodiment, the peptide comprises, consists essentially of, or consists of, (SEQ ID NO: 6)

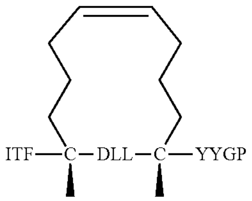

NYAD-1 wherein the (C)s are the α-carbons of the unnatural amino acids.

In another embodiment, the peptide comprises, consists essentially of, or consists of, (SEQ ID NO: 8)

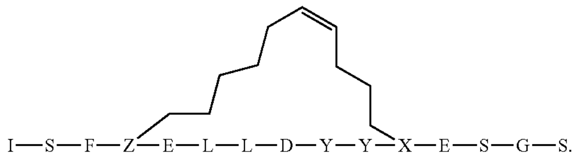

NYAD-36

The peptide NYAD-36 with a $R_{4,11}S(11)$ cross-link (FIG. 7) is a potent inhibitor of HIV-1 capsid assembly but is poorly soluble in pure $H_2O$ (<100 μM).

Exemplary embodiments of peptides according to the present disclosure are depicted in FIG. 7 and in SEQ ID NOs. 2-13 wherein X is (S)-α-2-(4'-pentenyl)alanine and Z is (S)-α-2-(7'-octanyl)alanine.

Since the peptides can enter cells, they can be used as a delivery system to deliver any additional useful moiety into the cell, for example for proteins, nucleic acids, carbohydrates, metals, etc. Where the peptides comprise an additional moiety to be delivered into the cell, the additional moiety is preferably a detectable moiety, a therapeutic compound, or an antigen. Preferred detectable moieties include fluorescent moieties and radioactive moieties. Where the peptide further comprises an antigen, the antigen can be anything that can elicit a useful immunological response. Non-limiting examples include viral antigens that can induce immunity to a virus and antigens that induce immunity to bacteria, for example *Mycobacterium tuberculosis*, or parasites, e.g., a *Plasmodium falciparum* antigen. A preferred viral antigen is an HIV antigen.

Where the moiety is a therapeutic compound, the compound can be any therapeutic compound now known or later discovered, and includes oligopeptides, for example less than 20 amino acids long, or less than 10 amino acids long. Preferred therapeutic compounds are organic compounds less than 2000 MW, for example an antiviral compound. Such therapeutic compounds can be, for example, in the form of a prodrug that is bound to the rest of the peptide with an ester bond that is susceptible to a cellular esterase, assuring that the therapeutic compound is not released until the peptide enters a cell. Methods of producing such prodrugs are known in the art.

As established in the Examples, the peptides can enter a cell and inhibit HIV reproduction. Without being bound to any particular mechanism, it is believed that the peptide binds to the capsid domain of the HIV gag protein, preventing viral assembly and thus replication. As such, the peptides are expected to bind and inhibit replication of any capsid-containing virus. Thus, preferred peptides can inhibit replication of a capsid-containing virus in a cell. Examples of capsid-containing viruses include the Retroviridae, including lentiviruses, such as HIV; Togaviridae including rubella virus; Picornaviridae such as enteroviruses, poliovirus, rhinovirus and hepatitis A virus; Orthomyxoviridae such as influenza virus; Paramyxoviridae such as paramyxoviruses; Herpesviridae such as herpes viruses and cytomegaloviruses; Hepnaviridae such as hepatitis B viruses; Flaviviridae such as flavivirus, hepatitis C virus, tick borne encephalitis, yellow fever and dengue fever viruses; Coronaviridae such as coronaviruses including SARS virus and toroviruses; Filoviridae such as Ebola and Marburg viruses; Bunyaviridae such as hantaviruses and arenaviruses.

The capsid-containing virus is preferably a retrovirus, e.g., HIV, HTLV-I, II and III, a feline immunodeficiency virus, a bovine immunodeficiency virus, a simian immunodeficiency virus, a feline sarcoma or leukemia virus, or a bovine leucosis virus.

In one embodiment, the peptide inhibits replication of a lentivirus. In certain embodiments, the peptide can inhibit replication of an HIV. It is expected that the peptides could inhibit any strain of HIV, including HIV-1 and HIV-2, since the Examples show that the peptide described above inhibits a wide range of HIV isolates (Table 1).

This disclosure is also directed to pharmaceutical compositions comprising the above-described peptides that can inhibit assembly of a capsid-containing virus, in a pharmaceutically acceptable carrier.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampoules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

This disclosure is additionally directed to methods of inhibiting replication of a capsid-containing virus in a cell. The methods comprise contacting the cell with the above-disclosed peptides that can inhibit a capsid-containing virus, in a manner sufficient to inhibit replication of the capsid-containing virus in the cell.

These methods are useful with any capsid-containing virus. Preferably the virus is a retrovirus, more preferably a lentivirus and most preferably an HIV.

Any prokaryotic, eukaryotic or archaea cell infected with a capsid-containing virus can be treated with the invention peptides. The method can utilize cells in culture (e.g., as in Examples), or preferably in a live multicellular organism, including any plants or animals. More preferably, the cell is part of a live vertebrate infected with the capsid-containing virus. Even more preferably, the cell is in a mammal infected with the capsid-containing virus. Still more preferably, the mammal is a human, most preferably infected with HIV.

Where the virus is in a live mammal, it is contemplated that the present methods could be used in conjunction with at least one other antiviral treatment, for example any antiviral treatment, or combination thereof, used against HIV, including, for example, but not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (CXCR4, CCR5) inhibitors and/or hydroxyurea.

Nucleoside reverse transcriptase inhibitors, include but are not limited to, Abacavir (ABC; ZIAGEN®), didanosine (dideoxyinosine (ddI); VIDEX®), lamivudine (3TC; EPIVIR®), stavudine (d4T; ZERIT®, ZERIT XR®), zalcitabine (dideoxycytidine (ddC); HIVID®), zidovudine (ZDV, formerly known as azidothymidine (AZT); RETROVIR®), abacavir, zidovudine, and lamivudine (TRIZIVIR®), zidovudine and lamivudine (COMBIVIR®), and emtricitabine (EMTRIVA®). Nucleotide reverse transcriptase inhibitors include tenofovir disoproxil fumarate (VIREAD®). Non-nucleoside reverse transcriptase inhibitors for HIV include, but are not limited to, nevirapine (VIRAMUNE®), delavirdine mesylate (RESCRIPTOR®), and efavirenz (SUSTIVA®).

Protease inhibitors (PIs) include amprenavir (AGENERASE®), saquinavir mesylate (FORTOVASE®, INVIRASE®), ritonavir (NORVIR®), indinavir sulfate (CRIXIVAN®), nelfmavir mesylate (VIRACEPT®), lopinavir and ritonavir (KALETRA®), atazanavir (REYATAZ®), and fosamprenavir (LEXIVA®). Atazanavir and fosamprenavir are new protease inhibitors that were recently approved by the U.S. Food and Drug Administration for treating HIV-1 infection (see atazanavir) and emtricitabine for HIV infection, Medical Letter on Drugs and Therapeutics, available online at www.medletter.com; U.S. Department of Health and Human Services (2003). Guidelines for the Use of Antiretroviral Agents in HIV-infected Adults and Adolescents; available online at aidsinfo.nih.gov/guidelines.

A fusion/entry inhibitor attaches to the outside of a CD4+ cell (a type of white blood cell) or coreceptors such as CCR5 and CXCR4 or to the viral membrane proteins, such as gp41 and gp120. Fusion/entry inhibitors prevent fusion between the virus and the cell from occurring or entry of the virus to the cells and therefore, prevent HIV infection and multiplication. Fusion/entry inhibitors include, but are not limited to, enfuvirtide (FUZEON®) and maraviroc (SELZENTRY®, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS®, Merck); and elvitegravir (GS 9137, Gilead Sciences).

Alternatively or additionally, the peptides disclosed herein may be administered in combination with one or more antiinfective agents (e.g., antibiotics, etc.), pain relievers, or other agents intended to address symptoms of one or more diseases, disorders, or conditions commonly found in immunocompromised individuals but not directly caused by HIV.

This disclosure is further directed to methods of treating a mammal infected with a capsid-containing virus. The methods comprise administering the above-described pharmaceutical composition to the mammal in a manner sufficient to treat the mammal. Preferably, the mammal is a human.

These methods are useful with any capsid-containing virus. Preferably the virus is a retrovirus, more preferably a lentivirus and most preferably an HIV.

In one embodiment, the peptide of these methods comprises (SEQ ID NO: 8)

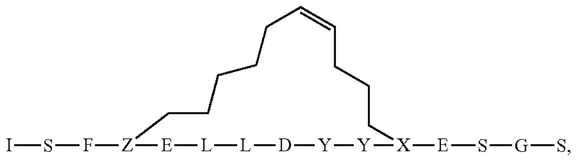

wherein X is (S)-α-2-(4'-pentenyl)alanine and Z is (S)-α-2-(7'-octanyl)alanine.

Some applications of these methods comprise treating a pregnant female infected with the virus to reduce the risk of passing the virus to the fetus in utero or to the baby during delivery.

It is contemplated that the present methods could be used in conjunction with at least one other antiviral treatment, for example any antiviral treatment, or combination thereof, used against HIV.

These methods can also be used as a prophylactic against infection with the capsid-containing virus. Thus, the present disclosure is additionally directed to methods of treating a mammal at risk for infection with a capsid-containing virus. The methods comprise administering the above-described pharmaceutical composition to the mammal in a manner sufficient to treat the mammal.

These methods are useful with any capsid-containing virus. Preferably the virus is a retrovirus, more preferably a lentivirus and most preferably an HIV.

Some applications of these methods comprise treating a fetus in utero having a mother that is infected with the virus to reduce the risk of passing the virus to the fetus in utero or to the baby during delivery.

It is also contemplated that the present methods could be used in conjunction with at least one other antiviral treatment, for example any antiviral treatment, or combination thereof, used against HIV, or any preventative antiviral treatment, including vaccination.

Further, disclosed herein are methods of making any of the above-described peptides. The methods comprise sequentially coupling the amino acids, then joining the two olefinic groups of the unnatural amino acids together using olefin metathesis. These methods are described in, e.g., Schafineister et al. (J. Am. Chem. Soc. 122:5891-5892, 2000); Walensky et al. (Science 305:1466-1470, 2004); United States Patent Application Publication 2006/0008848, and PCT Patent Application Publication WO 2005/044839. Preferably, the amino acids are coupled using solid phase synthesis.

The present disclosure is also directed to the use any of the above-described peptides that can inhibit assembly of a capsid-containing virus for the manufacture of a medicament for the treatment of a mammal infected with a capsid-containing virus.

Additionally, the present disclosure is directed to the use any of the above-described peptides that can inhibit assembly of a capsid-containing virus for the manufacture of a medicament for the treatment of a mammal to reduce the risk of the mammal becoming infected with a capsid-containing virus.

Also, disclosed herein are uses of the above-described pharmaceutical compositions for the treatment of a mammal infected with a capsid-containing virus.

This disclosure is additionally directed to the use of the above-described pharmaceutical compositions for the treatment of a mammal at risk for infection with a capsid-containing virus.

Certain embodiments disclosed herein are described in the following Examples. Other embodiments within the scope of the claims herein will be apparent to one skilled in the art from consideration of the specification. It is intended that the specification, together with the examples, be considered exemplary only, with the scope and spirit of the disclosure being indicated by the claims, which follow the examples.

EXAMPLES

The x-ray crystallographic structure of CAI (SEQ ID NO:1) bound to the C-CA was used in the rational modification of CAI using a structure-based approach to form a helical, metabolically stable and cell-penetrating constrained peptide (CPCP). It was reasoned that if the critical amino acids in the CAI that bind to the hydrophobic cleft of the C-CA were preserved and convert the linear peptide to a proteolytically stable cell penetrating peptide, the antiviral potency of the constrained peptide in in vivo could be achieved.

Cell permeability is a prerequisite for any drug to have in vivo activity if the target site is located inside the cell. The lack of cell permeability of peptide-based inhibitors restricts their utility in in vivo applications. Many techniques have been reported which enhance helix structures and metabolic stability of peptides. In some cases, improved binding affinities in in vitro assay have been reported. However, inhibitory potency in vivo or in cell-based assay were seldom reported indicating that these modifications may not render these peptides permeable to cells. Therefore, we resorted to a new and experimentally validated technique of stabilizing α-helicity of linear peptides reported by Schafineister et al. (Schafineister et al., 2000). This method was based on an all-hydrocarbon cross-linking system where the amino acids at the i and i+4 or i+7 of the helix were substituted by synthetically constrained amino acids bearing olefinic side chains, which were then cross-linked by olefin metathesis. This technique, termed "hydrocarbon stapling", has been recently successfully applied by Walensky et al. to a BCL-2 homology (BH) protein BH3 in activating apoptosis in vivo (Walensky et al., 2004). The helical and the metabolic stability of the constrained BH3 peptide not only increased substantially it also penetrated cells more efficiently and showed enhanced binding affinity to multidomain BCL-2.

Example 1

Peptide Synthesis

Asymmetric synthesis of (S)-Fmoc-2-(4'-pentenyl)alanine was prepared with Ala-Ni(II)-BPB-complex by the method of Qiu et al. (Tetrahedron 56:2577, 2000). The constrained peptide having the structure

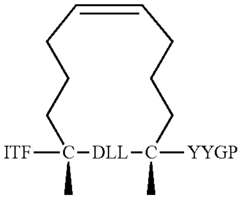

wherein the (C)s are the α-carbons of the unnatural amino acids. was synthesized manually by Fmoc solid phase synthesis method using Rink amide MBHA resin (0.33 mmol/g). For the normal amino acid, the couplings were performed with fourfold excess of activated amino acids. Fmoc-amino acids were activated using the ratio of Fmoc-amino acid: HBTU:HOBt:DIEA, 1:1:1:2. For (S)-Fmoc-2-(4'-pentenyl) alanine, couplings were performed with twofold excess of amino acid and activated using DIC:HOAt (1:1). For peptide olefin metathesis (Shafineister, et al., 2000), the peptide resin with N-terminal protected by Fmoc group was treated with degassed 1,2 dichloroethane containing Bis(tricyclohexylphosphine)benzylidine ruthenium (PV) dichloride (10 mM) at room temperature for two hr and the reaction was repeated once for completion. After de-Fmoc, the resin bound peptide was cleaved using standard protocols (95% TFA, 2.5% water, 2.5% TIS). The cleaved peptide was purified by RP-HPLC using 0.1% (v/v) TF A/water and 0.1% (v/v) TFA/acetonitrile and their identities were confirmed using electrospray mass spectroscopy.

For fluorescently labeled peptides, the N-terminal group of the above constrained peptide was further derivatized with β-Ala and FITC (DMF/DIEA) on the resin before the cleavage. The other cleavage, purification and confirmation steps were same as above.

Example 2

Assessment of Cellular Uptake of the Linear and the Constrained Peptides

In an initial experiment to show that the constrained peptides penetrate the cells, fluorescence-activated cell sorter (FACS) analysis was performed using two different cell types, 293T and MT-2 cells (FIG. 1). However, there are recent reports showing that the results in FACS analysis may not conclusively show whether the constrained peptides penetrated cells since peptides may associate with the cell surface. Therefore, a confocal microscopic study was performed to show conclusively that the constrained peptides NYAD-1 (FIG. 2) and NYAD-36 (FIGS. 13D-F) indeed penetrated the cell membrane and taken up by the cells whereas the linear peptides, FITC-CAI (FIG. 2) and 5FAM-β-Ala-NYAD-40 (FIG. 13B) did not penetrate. NYAD-40 (SEQ ID NO:19) is the linear analog of NYAD-36.

FACS Analysis of FITC-Conjugated Peptide-Treated Cells.

293T and MT2 cells were maintained in RPMI 1640 (Invitrogen), 10% fetal bovine serum, 100 U/ml penicillin, 100 μg/ml streptomycin, 2 mM glutamine, 50 mM HEPES pH 7, and 50 mM β-mercaptoethanol. Cells were seeded into a 24-well plate ($2\times10^4$/well) on the day before treatment with FITC-conjugated peptides. After two washes with 1×PBS, cells were incubated with 5 μM of FITC-conjugated peptide in serum-free medium for 4 hr at 37° C., and then washed three times with 1×PBS and digested with 0.25% trypsin for 30 min at 37° C. After one more wash with 1×PBS resuspended cells were subjected to FACS analysis (Becton Dickinson). The data indicate that about 40% and 96% of 293T cells were stained positive for FITC-conjugated CAI and for FITC-conjugated NYAD-1, respectively. In contrast, none of the MT-2 cells was stained positive for FITC-conjugated CAI whereas about 92% of MT-2 cells were stained positive for FITC-conjugated NYAD-1.

Confocal Microscopy.

Figure 2:
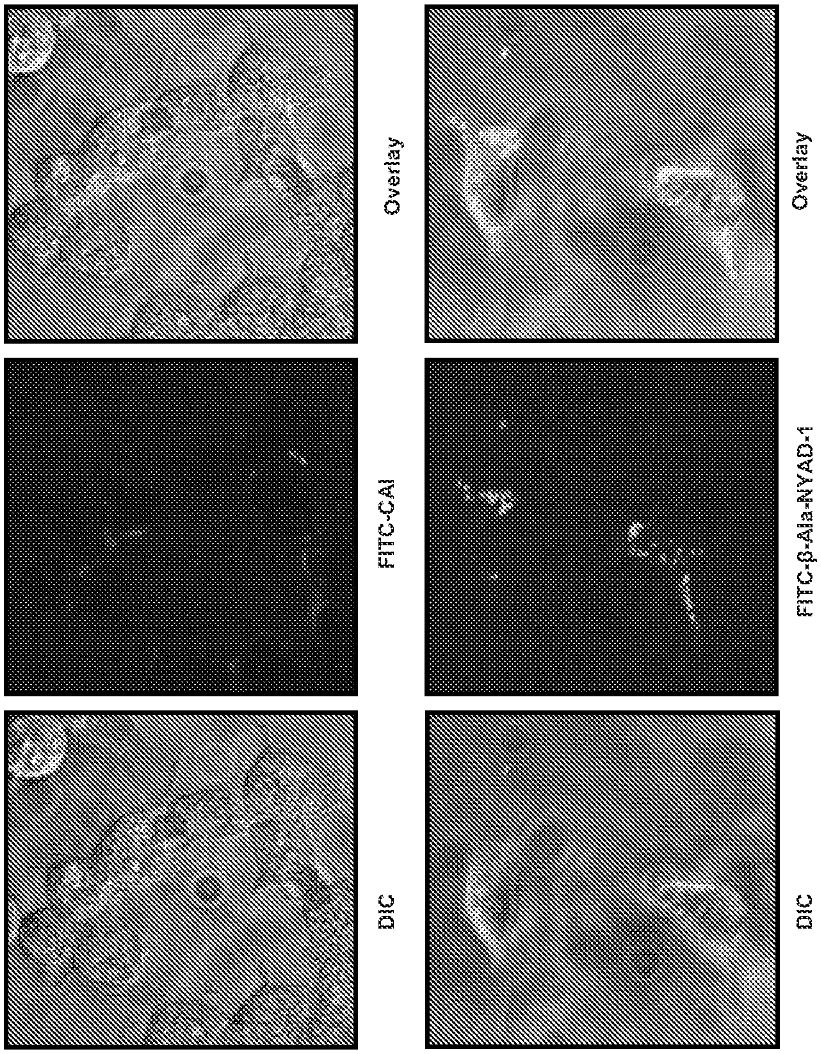
FIG. 2 depicts micrographs of cells showing that FITC-β-Ala-NYAD-1 penetrates 293T cells. Confocal microscopy images of 293T cells incubated for 20 hr at 37° C. with FITC-conjugated peptide. Cells were washed 3 times with PBS before viewing. Upper panel: Left, differential interference contrast (DIC) image of cells with FITC-CAI. Center, FITC fluorescent image of the same cells with FITC-CAI. Right, Overlay of DIC and FITC fluorescent images. Lower panel: Left, DIC image of cells with FITC-β-Ala-NYAD-1. Center, FITC fluorescent image of the same cells with FITC-β-Ala-NYAD-1. Right, Overlay of DIC and FITC fluorescent images.
Figures 13A, 13B, 13C, 13D, 13E, 13F:
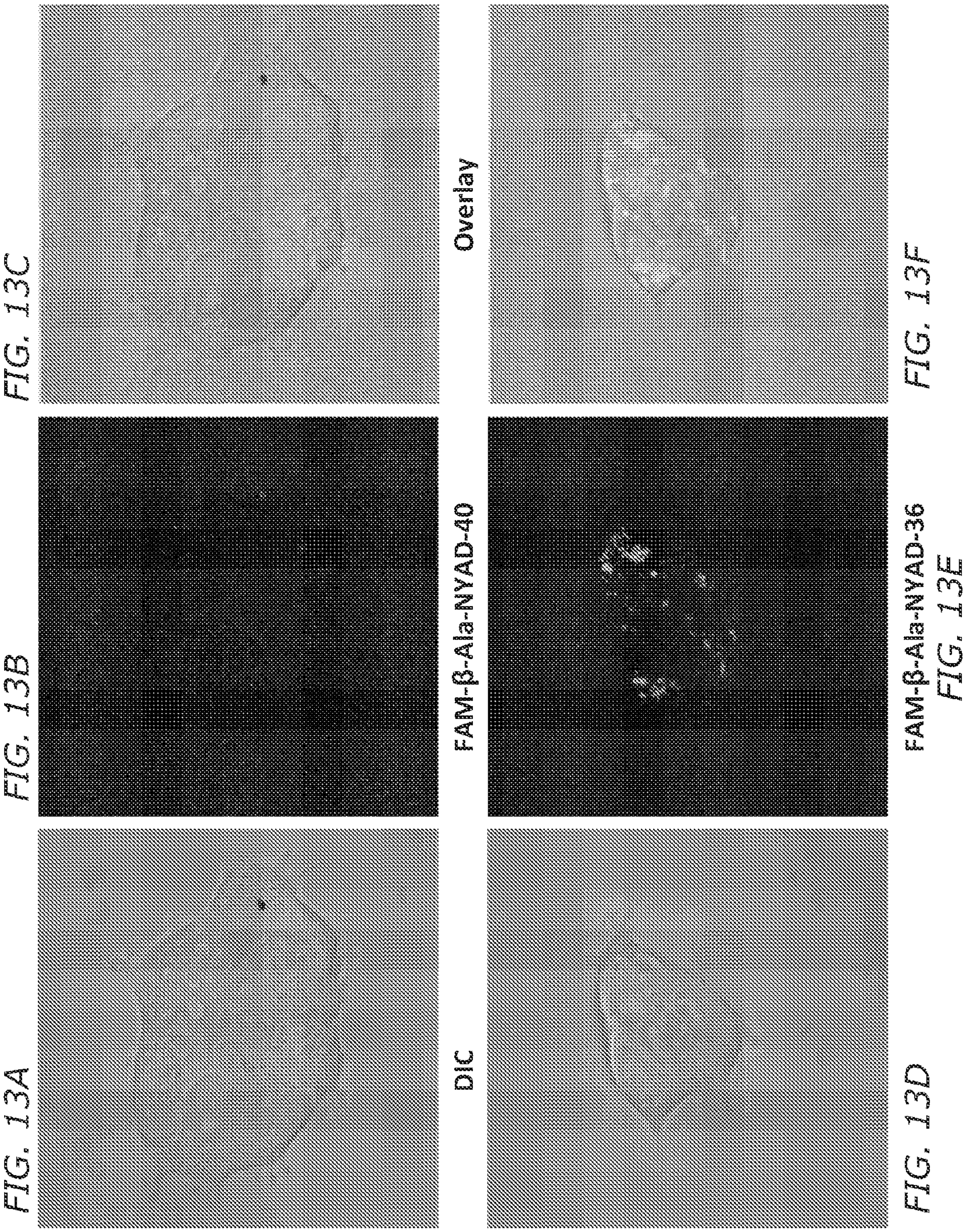
FIGS. 13A and 13D depicts DIC images of cells incubated with 6-carboxyfluorescein (FAM)-conjugated NYAD-41 and NYAD-36.
FIGS. 13B and 13E depict fluorescent images of the same cells in FIGS. 13A and 13D.
FIGS. 13C and 13F depict overlay of the DIC and fluorescent images.

293T and MT2 cells were seeded in the 4-well chamber plates and incubated with FITC-conjugated peptides as described above in serum-free medium for 4 hr and/or additional 16 hr in the complete medium containing serum. After 3 washes with 1×PBS, live cells were examined and imaged under confocal microscope (Zeiss). As shown in FIGS. 2 and 13, the constrained peptides NYAD-1 and NYAD-36 penetrated the cell membrane and was taken up by the cells, while the linear peptide FITC-CAI (FIG. 2) and FAM-β-Ala-NYAD-40 (FIG. 13B) did not penetrate.

Example 3

Inhibition of In Vitro Assembly

Both cell-free and cell-based methods were used to observe the morphological changes of virus like particles after treatment with CAI and NYAD-1.

Cell-Free System.

In vitro assembly systems were set up as described (Ganser-Pornillos, et al. J Virol 78:2545-2552, 2004; Huseby et al. J Biol. Chem. 280:17664-17670, 2005) with minor modification. We used 50 mM $Na_2HPO_4$, pH 8.0 as dialysis buffer. The buffer used for assembly studies also contained 0.1~2 M of NaCl. 500-Da-MWCO dialysis tubes (Spectra/Por) were used for the dialysis of peptides. Briefly, stock proteins were adjusted to the appropriate concentration (25 μM for gag proteins and 50 μM for CA proteins) with the $Na_2HPO_4$ buffer at pH 8.0. After addition of 5% total *E. coli* RNA (RNA: protein=1:20 by weight), incubation with or without 5-fold excess of CAI or NYAD-1 for 30 min at 4° C., the samples were dialyzed overnight in $Na_2HPO_4$ buffer at pH 8.0 containing 100 mM of NaCl at 4° C. For CA mature-like particles assembly, addition of 5% total *E. coli* RNA was omitted. Negative staining was used to check the assembly. To test the effect of inhibition on the assembled immature or mature virus like particles (VLPs), different concentrations of CAI or NYAD-1 were incubated with VLPs for 30 min at 4° C. Carbon-coated copper grids (200 mesh size; EM Sciences) were treated with 20 μl of poly-L-lysine (1 mg/ml; Sigma) for 2 min. 20 μl of reaction solution was placed onto the grid for 2 min. Spotted grids were then stained with 30 μl of uranyl acetate solution for 2 min. Excess stain was removed, and grids were air-dried. Specimens were examined with a Philips EM410 electron microscope.

Figure 4:
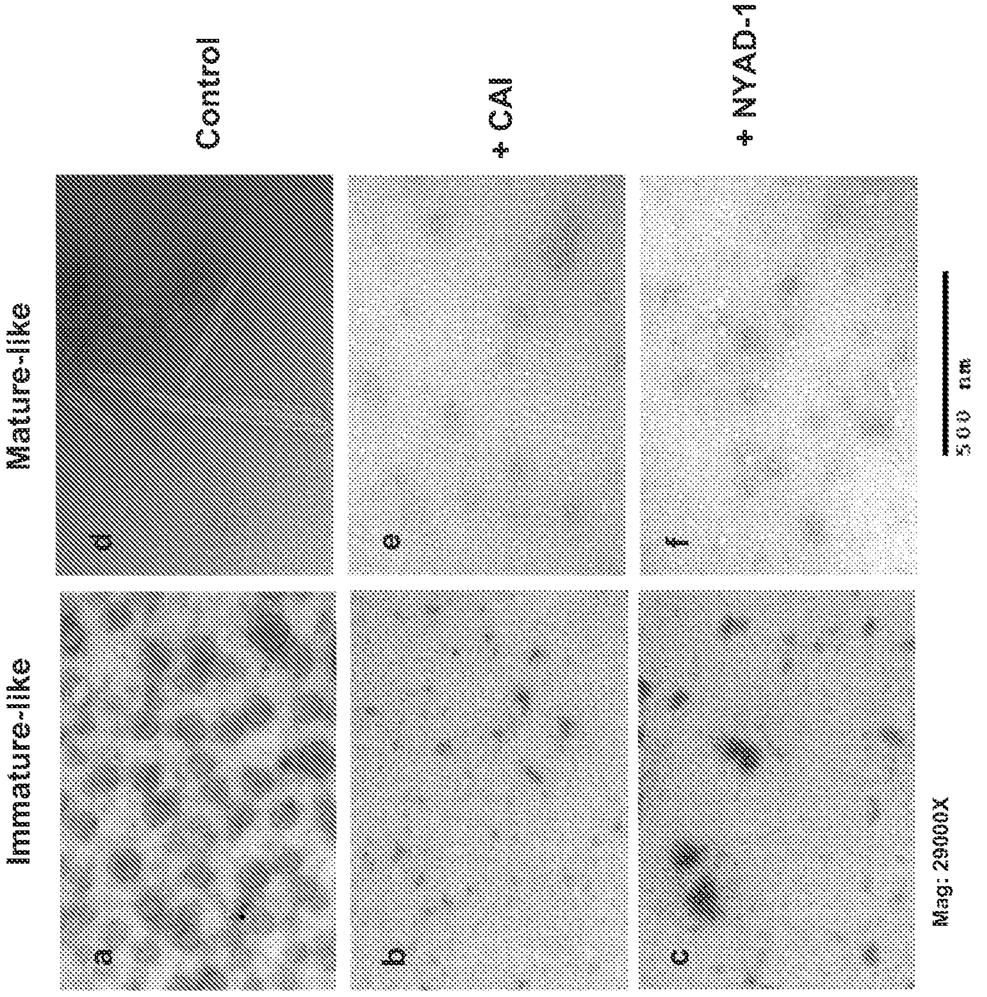
FIG. 4 depicts electron micrograph images showing the inhibition of assembly of immature-like and mature-like particles in vitro. The images are negatively stained EM images of particles resulting from in vitro assembly of gag and CA proteins, respectively, in the presence of none (control.

In order to verify whether NYAD-1 retains the ability to inhibit both immature and mature virus assembly we set up two in vitro assembly systems. We used full-length gag proteins to form spherical immature-like particles (FIG. 4A). After incubation with 5-fold molar excess of CAI or NYAD-1, the particles were completely disrupted (FIGS. 4B and 4C). For the mature-like particles, we expressed and purified CA protein and obtained tube-shaped particles (FIG. 4D). After incubation with 5-fold molar excess of either CAI or NYAD-1, the tube-shaped particles were completely disrupted (FIGS. 4E and 4F). The rationale for using CA instead of CANC to form the mature-like particles was to confirm that NYAD-1 targets CA only.

Inhibition of in vitro assembly was also compared between NYAD-36 (FIGS. 15A-E) and NYAD-1 (FIGS. 15F-J). FIG. 15 depicts negatively stained EM images of mature-like particles resulting from in vitro assembly of CA proteins in the presence of no peptide (FIGS. 15A and 15F) and 0.25—(FIGS. 15B and 15G), 0.5—(FIGS. 15C and 15H), 1.0—(FIGS. 15D and 15I), and 3.0—(FIG. 15E) and 5.0—(15J) fold molar equivalent of NYAD-1 or NYAD-36, respectively.

In an attempt to measure the inhibition of mature-like virus particle formation by NYAD-1 and NYAD-36, an in vitro experiment was conducted to form tube-like mature particles from purified CA protein. NYAD-1 at even 1-fold molar equivalent concentration completely disrupted the mature-like particle formation. In the case of NYAD-36, a slightly higher dose (5-fold molar equivalent) was required to achieve complete disruption. Nevertheless, both stapled peptides clearly showed their potential to disrupt mature-like particle formation, thereby virus assembly and maturation.

Cell-Based System.

To analyze the impacts of NYAD-1 on VLP release, and the morphology of VLPs, electron microscopy was conducted 1 day post-transfection with plasmid encoding gag or gag-pot. $4\times10^5$ 293T cells were seeded per well in a 6-well-plate on the day before transfection. Cells were washed twice after 4 hr transfection and incubated with complete culture medium in the presence or absence of NYAD-1 at different concentrations for another 20 hr. Cells were fixed in 3% gluteraldehyde in 100 mM sodium cacodylate for 1 hr and post-fixed in 1% $OsO_4$ in 100 mM sodium cacodylate for another 1 hr. Specimens were then dehydrated through graded series of ethanol solutions and embedded in EPON media. After staining with uranyl acetate and lead citrate, ultra-thin sections were examined under a Philips EM410 electron microscope at 80 Kv.

Figure 5:
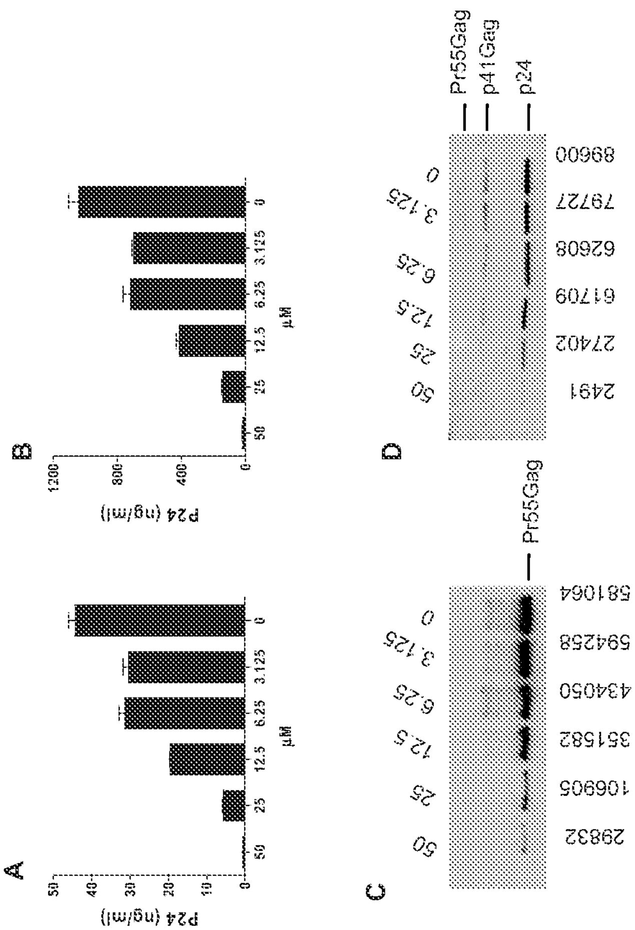
FIG. 5 depicts the effect of NYAD-1 on virus-like particle (VLP) release. 293T cells were treated with different concentrations of NYAD-1 4 hr post-transfection with a vector encoding gag (for immature-like particles) or gag-pol (for mature-like particles). The VLP-containing supernatant was recovered 48 hr post-transfection. The immature- and mature-like particle release was determined by measuring p24 by ELISA (FIGS. 5A and 5B) and Western Blot (FIGS. 5C and 5D). Numbers below the blots indicate the signal intensities obtained by densitometry.

To confirm that NYAD-1 disrupts immature- and mature-like particles in cells we employed ELISA, Western blot and electron microscopy (EM) to evaluate released particles both quantitatively and qualitatively. The ELISA results indicated a dose-dependent inhibition of the release of virus-like particles when gag-transfected 293T cells were treated with NYAD-1 at graded concentrations. At 50 μM dose about 72-fold reduction of the release of immature-like particles was observed compared to the untreated cells (FIG. 5A). A similar result (67-fold reduction) is obtained with gag-pol transfected 293T cells treated with NYAD-1 (FIG. 5B). The Western blot experiments performed with the supernatant also confirmed similar trends in inhibition of both gag—(FIG. 5C) and gag-pol-transfected cells treated with NYAD-1 (FIG. 5D).

Figure 6:
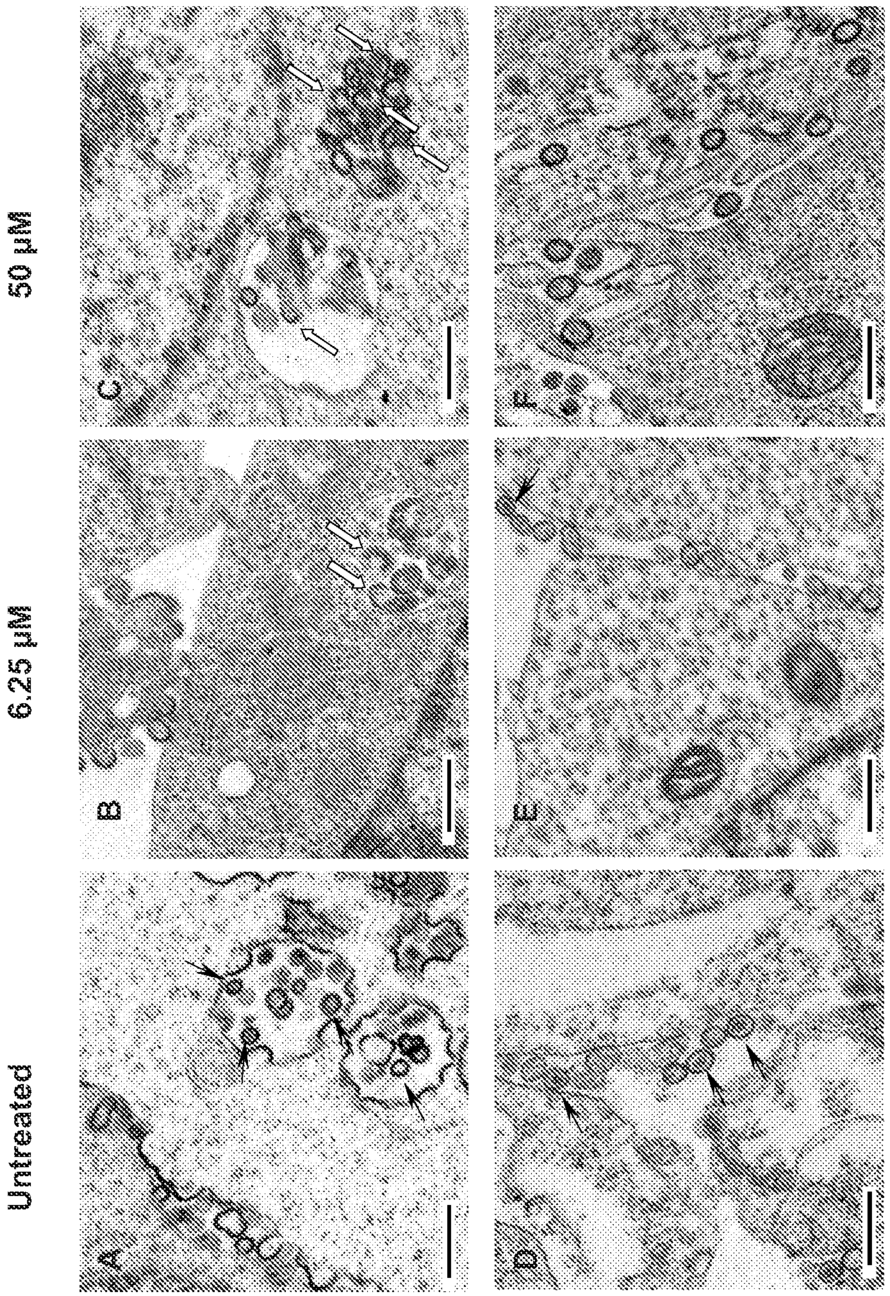
FIG. 6 depicts electron microscopic analysis of HIV-1 virus-like particles produced in the presence of 6.25 μM and 50 μM NYAD-1. 293T cells expressing gag (FIGS. 6A-6C) or gag-pol (FIG. 6D-6F) were incubated with 2 ml culture medium containing none, 6.25 uM, or 50 μM of NYAD-1 4 hr post-transfection with vector encoding gag or gag-pol. 24 hr post-transfection, cells were pelleted, fixed, embedded, sectioned, and examined with a transmission electron microscope. (Bar=500 nm.)
Figure 7A:
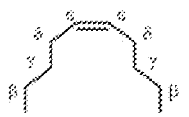
FIG. 7 depicts the amino acid sequences of selected peptides. Z=(R)-α-2-(7'-octenyl)alanine; X==(S)-α-2-(4'-pentenyl)alanine.
Figure 7A:
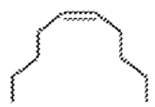
Figure 7A:
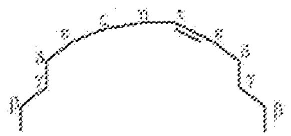
Figure 7A:
Figure 7B:
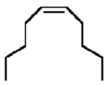
Figure 7B:
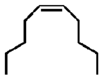
Figure 7B:
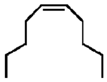
Figure 7B:
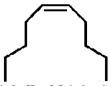
Figure 7B:
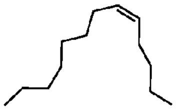
Figure 7B:
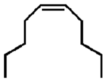
Figure 7B:
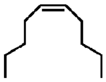
Figure 7B:
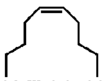
Figure 8:
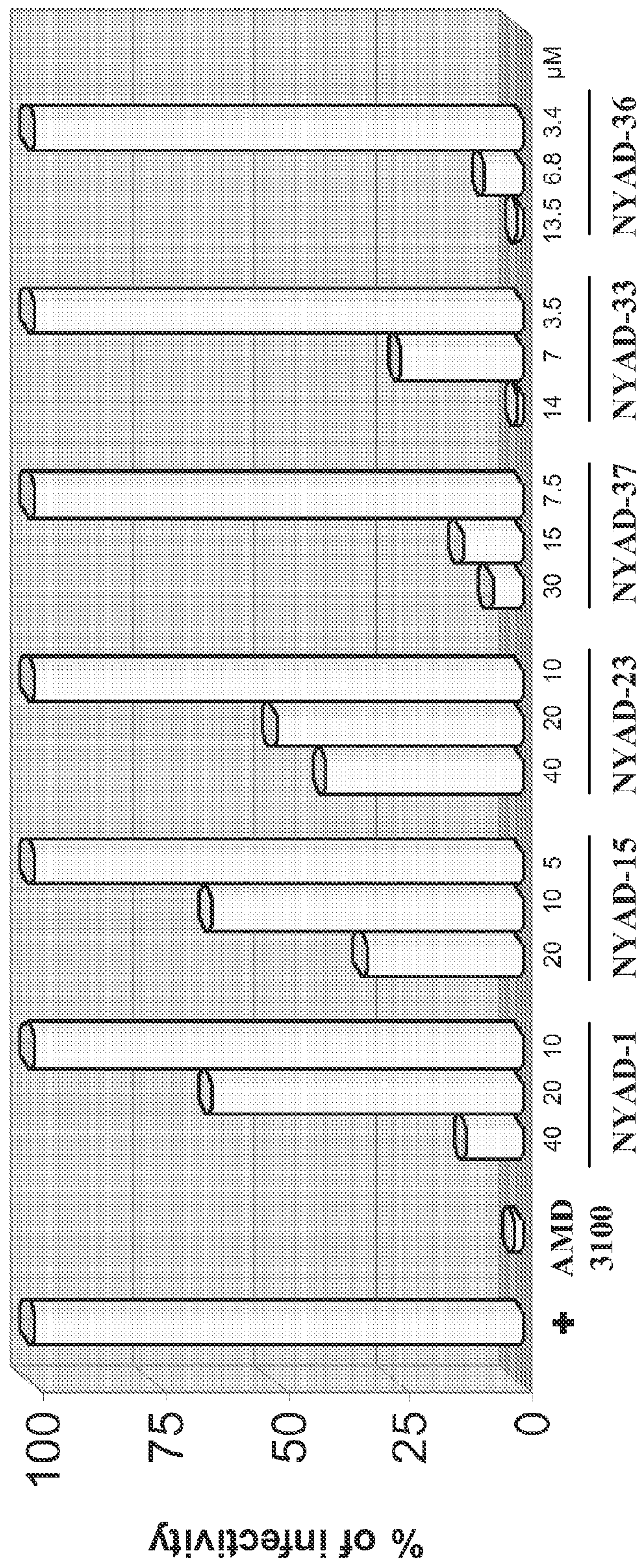
FIG. 8 depicts the effects of NYAD-1, -15, -23, -37, -33 and -36 in a viral re-infection assay.

Electron microscopic analysis of the untreated gag-transfected 293T cells showed distinct immature-like particles (FIG. 6A). However, when the cells were treated with 6.25 or 50 μM NYAD-1, a majority of the particles have an aberrant shape (FIGS. 6B and 6C). In case of untreated gag-pol transfected 293T cells, a large number of mature-like particles containing electrodense core structures were found (FIG. 6D). When these cells were treated with 6.25 or 50 μM NYAD-1 the electrodense core structures were lost in the released VLPs (FIGS. 6E and 6F). Taken together, these data confirm that NYAD-1 targets gag and impairs the organization of gag or its products at the cellular level.

Example 4

Inhibition of Viral Replication and Assessment of In Vitro Cytotoxicity

MT-2 and PBMC cells and several laboratory-adapted strain of HIV-1, such as HIV-1 IIIB, BaL, SF2, SF162, 93N101, 93US657, 93MW959, 92RW008, etc, including AZT-resistant isolates, were used for the virus inhibition assays. Cell lines and the HIV-1 strains can be obtained through the NIH AIDS Research and Reference Reagent Program.

The inhibitory activity of the constrained peptide described in Example 1 on infection by laboratory-adapted HIV-1 strains was determined as described in Jiang et al. (1991). In brief, $1\times10^4$ MT-2 cells were infected with HIV-1 at 100 $TCED_{50}$ (50% tissue culture infective dose) (0.01 MOD in 200 μl RPMI 1640 medium containing 10% FBS in the presence or absence of peptides at graded concentrations overnight. The culture supernatant was then removed and fresh media was added. On the fourth day post-infection, 100 μl of culture supernatants was collected from each well, mixed with equal volumes of 5% Triton X-100 and assayed for p24 antigen by ELISA using a kit from Coulter Immunology and presented in Table 1.

Inhibitory activity of the peptides on infection by primary HIV-1 isolates was determined by the method described in Jiang et al. (Antimicrobial Agents and Chemotherapy 48:4349-4359, 2004). PBMCs were isolated from the blood of healthy donors at the New York Blood Center by standard density gradient centrifugation using Histopaque-1077 (Sigma). The cells were cultured at 37° C. for 2 hr. The nonadherent cells were collected and resuspended at $5\times10^6$ cells/ml RPMI-1640 medium containing 10% FBS, 5 μg/ml PHA and 100 U/ml IL-2 (Sigma-Aldrich), followed by incubation at 37° C. for 3 days. The PHA-stimulated cells ($5\times10^4$) were infected with corresponding primary HIV-1 isolates at 500 $TCID_{50}$ in the absence or presence of peptides at graded concentrations. Culture media were changed every 3 days. The supernatants were collected 7 days post-infection and tested for p24 antigen by ELISA. The percent inhibition of p24 production was calculated and $IC_{50}$ values were calculated using the GraphPad Prism software (GraphPad Software Inc.) and presented in Table 1.

The in vitro cytotoxicity of the constrained peptide in MT-2 cells and PBMCs was measured by a colorimetric method using XTT (sodium 3'-(1-(phenylamino)-carbonyl)-3,4-tetrazolium-bis(4-methoxy-6-nitro)benzenesulfonic acid hydrate), a light yellowish tetrazolium dye. Briefly, for MT-2 cells, 100 μl of a peptide at graded concentrations was added to equal volume of cells ($5\times10^5$/ml) in wells of 96-well plates followed by incubation at 37° C. for 4 days, which was run in parallel to the neutralization assay in MT-2 with only difference of adding medium instead of virus. In the case of PBMC, $5\times10^5$ cells/ml were used and the cytotoxicity was measured after 7 days. After addition of XTT (PolySciences, Inc), the soluble intracellular formazan was quantitated colorimetrically at 450 nm 4 hr later with a reference at 620 nm. The percent of cytotoxicity and the $CC_{50}$ (the concentration for 50% cytotoxicity) values were calculated using the GraphPad Prism software and listed in Table 1.

NYAD-1 showed inhibition of both immature- and mature-like particles in cell-free as well as cell-based assembly systems. However, our goal was to confirm its anti-HIV-1 activity in a cell-based assay using several laboratory-adapted and primary isolates in MT-2 cells and PBMC, respectively. The inhibition of p24 production in MT-2 cells by NYAD-1 was measured over a range of concentrations and the concentration required to inhibit 50% of the p24 production ($IC_{50}$) was calculated. The results in Table 1 indicate that NYAD-1 efficiently inhibited a broad range of HIV-1 strains, representing different subtypes, which use R5, X4 or R5X4 coreceptors. NYAD-1 inhibited the laboratory strains with low μM potency ($IC_{50}$~4-15 μM), and both R5- and X4-tropic viruses were inhibited with similar potency. We also tested one X4-tropic RT-resistant (AZT) strain in MT-2 and one dual tropic (R5X4) RT-resistant (AZT) strain in PBMC and NYAD-1 inhibited the dual-tropic resistant virus with slightly higher potency.

We tested the inhibition of NYAD-1 against a panel of HIV-1 primary isolates in PBMC representing mostly group M (subtypes from A to G) with diverse coreceptor usage. NYAD-1 showed inhibition against all primary isolates tested including one from group O (Table 1). However, the $IC_{50}$ values against this virus (BCF02) as well as one from Glade E (93TH051) were slightly higher. The inhibitory activities against this diverse range of primary isolates were similar indicating its effectiveness against a wide range of HIV-1 isolates.

The cytotoxicity of NYAD-1 was assessed by the XTT method in both MT-2 cells and PBMC. Cytotoxicity assays were performed in parallel to the HIV-1 inhibition assays. The $CC_{50}$ (concentration of inhibitor required to produce 50% cytotoxicity) values for MT-2 and PBMC were >135 and >300 μM, respectively.

TABLE 1

Antiviral activity of the constrained peptide NYAD-1 in laboratory primary HIV-1 isolates

| HIV-1 Virus | Primary Clade | Cell Type | Coreceptor use | $IC_{50}$ (μM) ± SD |
|---|---|---|---|---|
| Laboratory-Adapted | | | | |
| IIIB | B | MT-2 | X4 | 6.22 ± 0.75 |
| MN | B | MT-2 | X4 | 6.79 ± 0.65 |
| RF | B | MT-2 | X4 | 4.29 ± 0.42 |
| V32 | B | MT-2 | X4 | 7.91 ± 0.70 |
| BaL | B | PBMC | X4 | 6.47 ± 0.85 |
| SF162 | B | PBMC | R5 | 15.44 ± 3.23 |
| AZT-Resistant | | | | |
| AZT-R | B | MT-2 | X4 | 16.28 ± 2.79 |
| A17 | B | PBMC | R5X4 | 10.55 ± 1.56 |
| Primary Isolates | | | | |
| 92RW008 | A | PBMC | R5 | 12.12 ± 1.64 |
| 92UG029 | A | PBMC | X4 | 13.85 ± 1.34 |
| 92US657 | B | PBMC | R5 | 10.54 ± 2.78 |
| 93IN101 | C | PBMC | R5 | 16.48 ± 0.47 |
| 93MW959 | C | PBMC | R5 | 16.49 ± 2.83 |
| 92UG001 | D | PBMC | R5X4 | 9.14 ± 0.27 |
| CMU02 | E | PBMC | X4 | 10.03 ± 0.81 |
| 93TH051 | E | PBMC | R5X4 | 20.50 ± 1.90 |
| 93BR020 | F | PBMC | R5X4 | 6.60 ± 1.60 |
| RU570 | G | PBMC | R5 | 9.79 ± 2.49 |
| BCF02 | (Group O) | PBMC | R5 | 21.60 ± 3.04 |

The linear peptide CAI did not show any activity up to 200 μM dose level. The $CC_{50}$ value in MT-2 cells was >135 μM; and in PBMC cells was >300 μM.

Example 5

Hydrocarbon Stapling Enhanced α-Helicity

We used circular dichroism (CD) to characterize the secondary structure of NYAD-1 and CAI in the uncomplexed state in solution. CD spectra were obtained on a Jasco J-715 Spectropolarimeter (Jasco Inc.) at 20° C. using the standard measurement parameters in Tris-HCl buffer (20 mM Tris, pH 8.0) in the presence of 1-15% (v/v) acetonitrile at a final concentration of 125-500 μM. In all the samples, the final concentrations of peptides and salt were always the same, and the spectra were corrected by subtracting the CD spectra of the appropriate reference solvent. Percent α-helix was calculated from molar ellipticity [θ] value at 222 nm. The CD spectrum of CAI did not show typical helix minima at 222 and 208 nm, rather a strong minimum at 205 nm was observed indicative of random coil structure in solution. This supports a binding induced conformational change of the CAI peptide in complex with C-CA. In contrast, the CD spectrum of NYAD-1 showed distinct minima at both 222 and 208 nm. The α-helicity of NYAD-1, calculated from the molar elipticity value at 222 nm, is ~80%. The results confirm our hypothesis that hydrocarbon stapling enhances the α-helicity of CAI.

Figure 12:
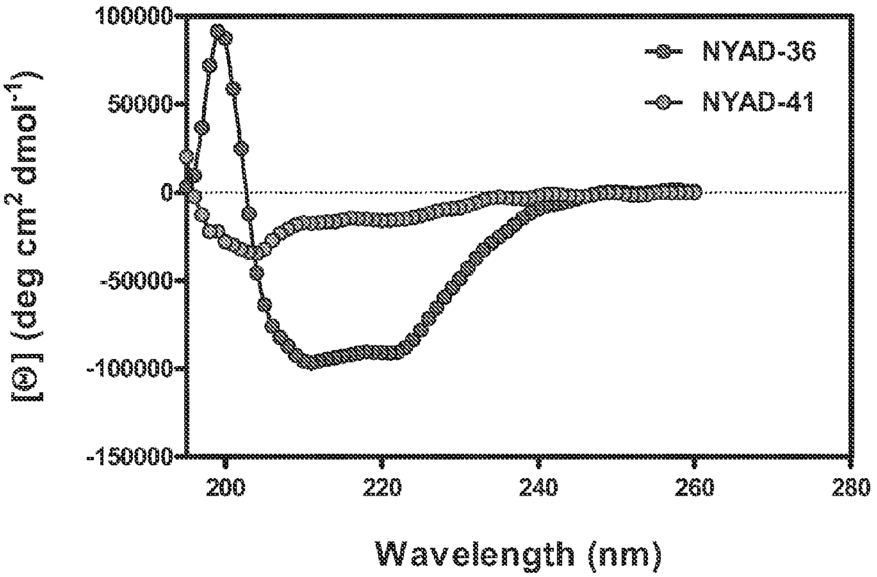
FIG. 12 depicts the circular dichroism (CD) spectra of NYAD-41 and NYAD-36.

The circular dichroism (CD) spectra of NYAD-36 and NYAD-41 (SEQ ID NO:20) were also determined. The CD spectra were measured at 25° C. in 1×PBS in the presence of 1-20% (v/v) acetonitrile at a final concentration of peptide of 100 μM. NYAD-36 demonstrated typical wavelength minima at 208 and 222 nm, whereas NYAD-41 showed a minimum at 205 nm (FIG. 12).

We used CD spectroscopy to determine the secondary structure characteristics of the stapled peptide NYAD-36. The corresponding linear peptide, NYAD-41, was used as control. The CD spectra of NYAD-36 showed two typical minima at 208 and 222 nm indicative of its α-helical structure, whereas the linear peptide, NYAD-41, did not show such minima indicating its random nature.

Example 6

NYAD-1 Colocalizes with HIV-1 gag

Figure 3:
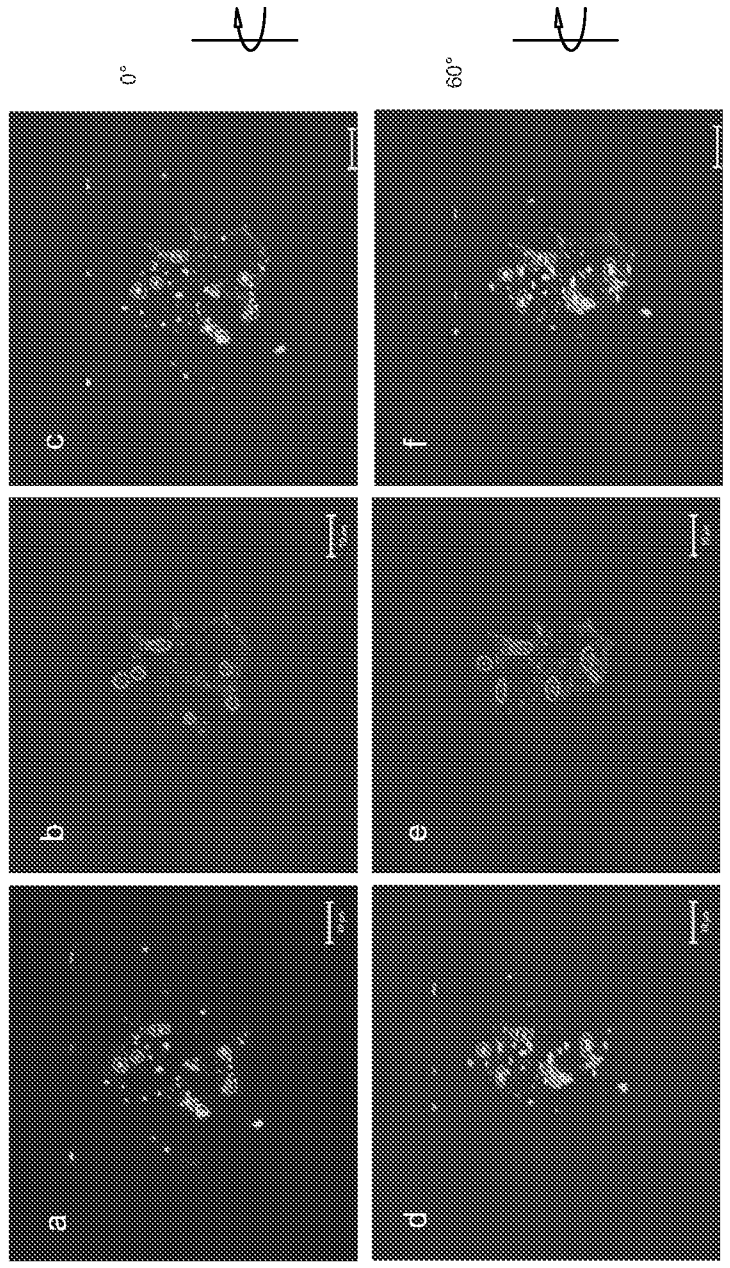
FIG. 3 depicts a direct colocalization study of NYAD-1 and gag by confocal microscopy. Images at different angles were shown.

Although NYAD-1 penetrates cells it does not guarantee that it will colocalize and interact with the gag polyprotein to inhibit viral assembly. To address this concern, we performed a direct colocalization experiment using HIV-1 gag-mStrawberry fusion protein and FITC-conjugated NYAD-1. A direct colocalization study was performed by transfecting 293T cells with pEF6A-gag-mStrawberry for 4 hr and then washing cells once with PBS. A serum-free or serum-containing medium containing FITC-conjugated peptide was added for another 20 hr culture. After three washes, the cells were examined and imaged under a Zeiss LSM510 laser scanning confocal microscope. When gag-mStrawberry transfected cells were exposed to the FITC-conjugated NYAD-1, significant fraction colocalized (FIG. 3, data shown at two different angles) near the plasma membrane. The colocalization data firmly establish the cell permeability of NYAD-1 and suggest interactions with the gag polyprotein.

Example 7

Infectivity Potential of Self-Associating Stapled Peptides on

The infectivity potential of the virions released by HIV-1 infected MT-2 cells treated with different concentrations of small stapled peptides. $5\times10^4$/ml MT-2 cells were infected with HIV-IIIB (m.o.i.=0.01) in the presence of 3 different concentrations of small peptides NYAD-1, -15, -23, -37, -33 and -36. Control cells were untreated or treated with 1 ug/ml of AMD3100 (CXCR-4 receptor inhibitor). Following overnight incubation the medium was completely removed and replaced with fresh medium. On the fourth day post-infection the supernatants were collected. One aliquot of each sample was mixed 1:1 with a solution of 5% Triton X-100 for p24 quantification, and stored at 4° C., another aliquot was immediately frozen at −80° C. and used to compare the infectivity of the viral particles released by treated cells to the viral particles released by untreated cells. Following p24 quantification by sandwich-ELISA MT-2 cells were infected with viral samples normalized for the p24 content to calculate the $TCID_{50}$. Following overnight incubation ¾ of the medium containing the inoculum was replaced with fresh medium. On the fourth day post infection supernatants were collected for p24 quantification and the $TCID_{50}$ was calculated by the Spearman-Karber statistical method. Viral infectivity is showed as percentage with respect to the positive untreated control.

Antiviral assays have shown a decrease in HIV-1 viral particle release by cells treated with small stapled peptides represented by reduction in p24 production. We believe that these peptides may be interfering with viral uncoating and viral assembly/maturation inducing irreparable damage to the viral particles newly produced and released in the supernatant, therefore, making them less infectious. To support our hypothesis, p24 normalized virus-containing supernatants were titered on MT-2 cells to calculate $TCID_{50}$. However, at higher doses of peptides or in supernatant of AMD3100-treated cells, we could detect very little to no p24. Therefore, to infect MT-2 cells we used the maximum quantities of supernatants possible. We calculated the $TCID_{50}$ considering only those doses which showed measurable infectivity. We detected very little to no viral infectivity for samples treated with AMD3100, 40 μM of NYAD-1, 30 and 15 μM of NYAD-37, 14 and 7 μM of NYAD-33 and 13.5 and 6.8 μM of NYAD-36. We detected 30-60% of infectivity respect to the control in the viral particles produced by the cells treated with 20 μM of NYAD-1, 20 and 10 μM of NYAD-15, 40 and 20 μM of NYAD-23. The most effective peptides were NYAD-33 and NYAD-36 in fact with about 7 μM we detected a 25% and 7.7% of infectivity only. Taken together these results suggest that the cells treated with these peptides produce less infectious viruses; therefore, these molecules interfere with viral assembly and/or maturation.

TABLE 2

Antiviral activity of constrained peptides against laboratory isolate HIV-1 IIIB in MT-2 cells

| Peptide | $IC_{50}$ (μM) ± SD |
|---|---|
| NYAD-15 | 4.86 ± 1.55 |
| NYAD-23 | 9.10 ± 0.74 |
| NYAD-24 | 13.80 ± 3.57 |
| NYAD-31 | 13.50 ± 1.40 |
| NYAD-33 | 3.37 ± 0.06 |
| NYAD-34 | 12.70 ± 0.90 |
| NYAD-35 | 4.51 ± 0.14 |
| NYAD-36 | 1.50 ± 0.17 |
| NYAD-37 | 8.00 ± 0.36 |

Example 8

Detection of Viral and Cellular Proteins after Treatment with Stapled Peptides $5\times10^4$/ml MT-2 cells were infected with HIV-1 IIIB (m.o.i.=0.01) in the presence of different concentrations of stapled peptide NYAD-1 (30, 15 and 7.5 μM), NYAD-15 (20, 10 and 5 μM), NYAD-23 (40, 20 and 10p), NYAD-37 (30, 15 and 7.5 μM) and NYAD-36 (10.8, 5.4, 2.7 and 1.3 μM). Control cells were uninfected MT-2 or infected and untreated MT-2. Following overnight incubation the culture supernatant was completely removed and replaced with fresh medium. On the fourth day post-infection cells and virus supernatants were harvested. The supernatants were filtered and ultra-centrifuged through a 20% sucrose cushion for 2 hr at 27,000 rpm with a SW28 rotor to concentrate the viral particles. Viral pellets were slowly re-suspended and lysed. Cells were collected and processed for protein extraction. Same volume of viral lysates and cellular lysates were resolved on a NuPAGE Novex 4-12% Bis-Tris Gel (Invitrogen). Proteins were then visualized by Western Blot and immuno-detected with HIV-1 anti-p24 gag mAb.

Figure 9A:
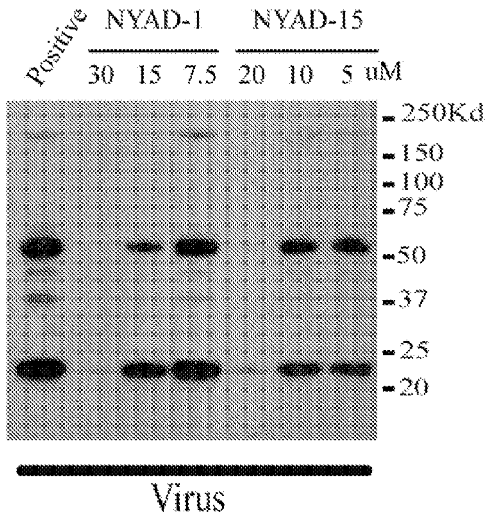
FIG. 9A depicts the effects on viral-infected calls and FIG. 9B depicts the effects on uninfected cells.
Figure 9B:
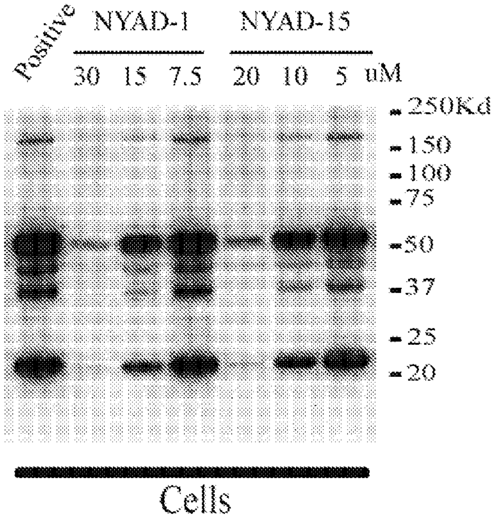
Figure 10A:
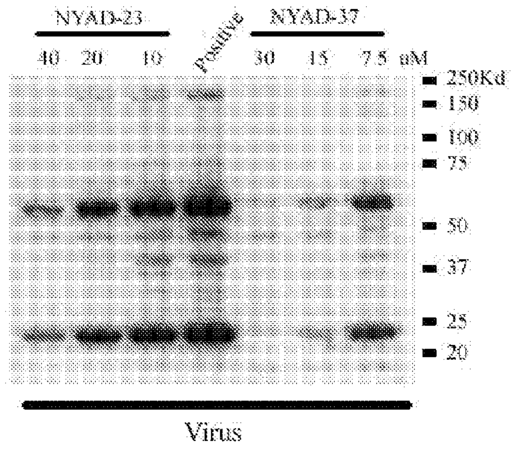
FIG. 10A depicts the effects on viral-infected calls and FIG. 10B depicts the effects on uninfected cells.
Figure 10B:
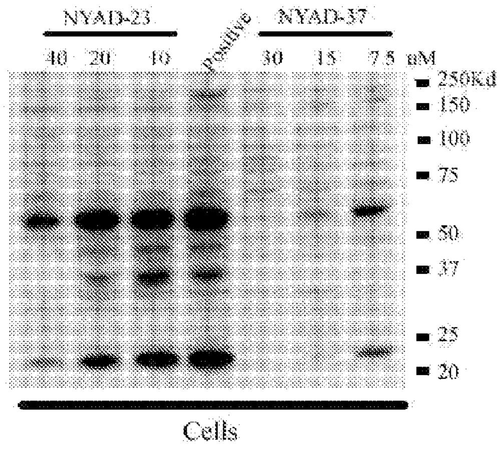
Figure 11A:
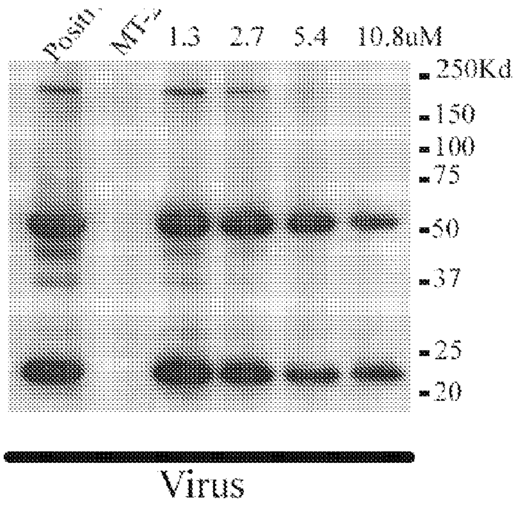
FIG. 11A depicts the effects on viral-infected calls and FIG. 11B depicts the effects on uninfected cells.
Figure 11B:
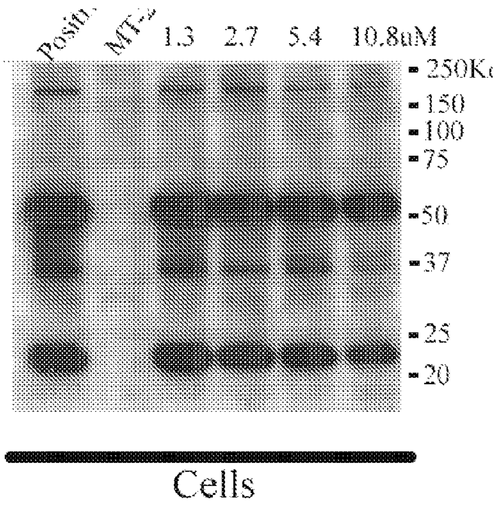

Same amounts of viral and cellular proteins were immunodetected with an anti-p24 mAb. FIGS. 9 and 10 demonstrate that treatment with NYAD-1, -15, -23, and -37 induced a dose-dependent decrease in p24 and p55 levels with respect to the positive untreated control in both viral and cellular preparation confirming the data obtained with the neutralization experiments. Also, while treatment with NYAD-36 induced an obvious dose-dependent decrease in p24 and p55 levels in the viral lysates but the same decrease was not detected in the cellular preparation (FIG. 11). These results suggest that NYAD-36 may be also preventing viral budding.

Example 9

Isothermal Titration Microcalorimetric Analysis

Isothermal titration calorimetry (ITC) was used to measure the binding affinity of NYAD-36 with the CTD of capsid. Since, CTD has a tendency to form dimers in solution, a mutant version of CTD was used which was shown to exist as monomer.

Figure 14:
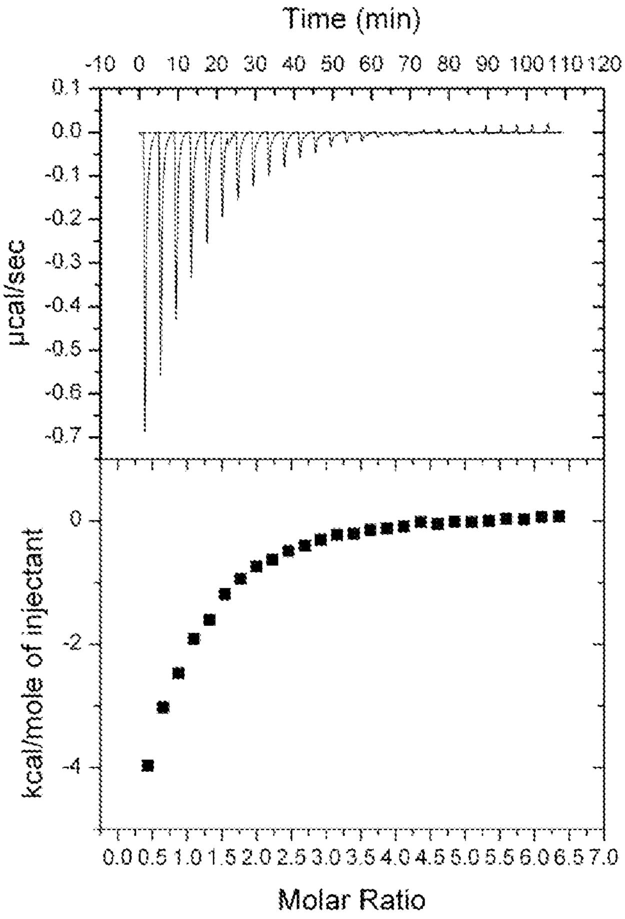
FIG. 14 depicts isothermal titration microcalorimetric analysis of CTDM184A/W185A/NYAD-36 interaction.
Figure 15A:
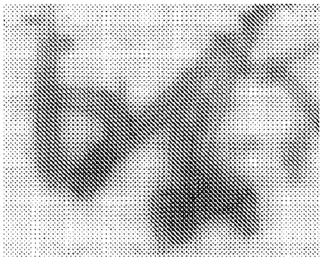
FIG. 15 depicts inhibition of in vitro viral assembly by NYAD-36 and NYAD-1.
Figure 15B:
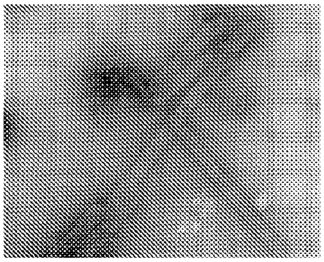
Figure 15C:
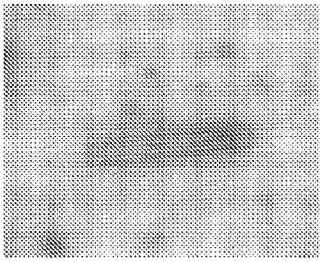
Figure 15D:
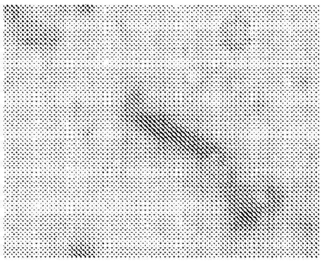
Figure 15E:
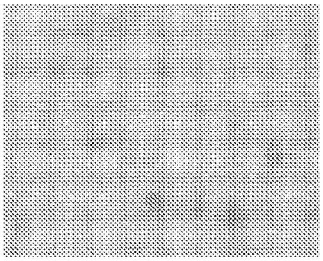
Figure 15F:
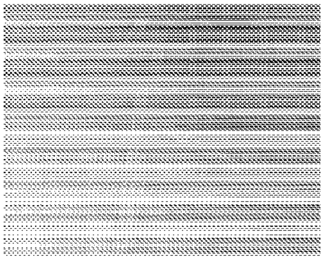
Figure 15G:
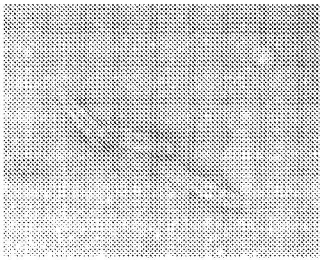
Figure 15H:
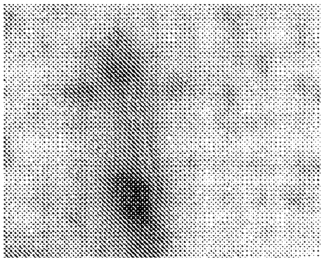
Figure 15I:
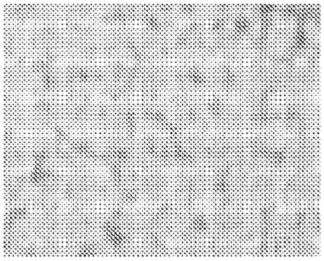
Figure 15J:
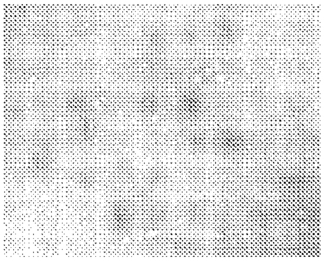

The binding affinity between CTDM184A/W185A and NYAD-36 was investigated by ITC (MicroCal VP-ITC). Both CTDM184A/W185A protein and NYAD-36 peptide were exhaustively dialyzed against 25 mM sodium phosphate buffer (pH 7.3) prior to experimental measurements. In a typical experiment, the ITC injection syringe was loaded with 625 μM CTDM184A/W185A protein dissolved in the dialysis buffer. The calorimetric cell (ca. 1.4 ml active volume) initially contained only 25 μM NYAD-36 in the identical dialysis buffer. Typically titrations consisted of 27 injections of 10 μl into the calorimetric cell, with 240-s equilibration between injections. The thermodynamic parameters were obtained and data were analysed using MicroCal Origin 7.0 software. The integrated binding isotherm (FIG. 14) was fit to a single-binding model, yielding a CTDM184A/W185A to NYAD-36 binding ratio of 0.75 (±0.03), Kd=11 (±0.3) μM, and ΔH=−8.4 (±0.4) Kcal/mol. The data indicates that NYAD-36 binds to mutant CTD with low μM binding affinity.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A peptide comprising an amino acid sequence I(T/S)FE(D/E)(L/I/W)L(D/Q)YY (SEQ ID NO:21), wherein two of the amino acids are substituted with unnatural amino acids (S)-α-2-(4'-pentenyl)alanine or (S)-α-2-(7'-octanyl)alanine, wherein olefinic groups of the unnatural amino acids are on the same side of the α-helix and are joined to form a cross-link between the two unnatural amino acids, wherein the two unnatural amino acids replace two of the amino acids at positions four amino acids apart (i and i+4) or seven amino acids apart (i and i+7), and the amino acid sequence is one of SEQ ID NOs:7-9 or 11-18.

2. The peptide of claim 1 wherein the amino acid sequence is SEQ ID NO:8.

3. The peptide of claim 1, further comprising a detectable moiety, a therapeutic compound, or an antigen.

4. The peptide of claim 3, wherein the detectable moiety, therapeutic compound, or antigen is a fluorescent moiety or a radioactive moiety.

5. The peptide of claim 3, wherein the detectable moiety, therapeutic compound, or antigen is an antigen.

6. The peptide of claim 5, wherein the antigen is human immunodeficiency virus antigen.

7. The peptide of claim 3, wherein the detectable moiety, therapeutic compound, or antigen is a therapeutic compound.

8. The peptide of claim 7, wherein the therapeutic compound comprises an oligopeptide less than 20 amino acids long.

9. The peptide of claim 7, wherein the therapeutic compound is an organic compound less than 2000 MW.

10. The peptide of claim 9, wherein the organic compound is an antiviral compound.

11. A method of treating a mammal infected with a human immunodeficiency virus, comprising administering a pharmaceutical formulation comprising the peptide of claim 1 in a manner sufficient to treat the mammal.

12. The method of claim 11, further comprising treating the mammal with at least one additional anti-viral agent.

* * * * *

SEQUENCE LISTING

```
<160> NUMBER OF SEQ ID NOS: 26

<210> SEQ ID NO 1
<211> LENGTH: 12
<212> TYPE: PRT
<213> ORGANISM: Artificial
<220> FEATURE:
<223> OTHER INFORMATION: Synthetic peptide CA1

<400> SEQUENCE: 1

Ile Thr Phe Glu Asp Leu Leu Asp Tyr Tyr Gly Pro
1               5                   10


<210> SEQ ID NO 2
<211> LENGTH: 10
<212> TYPE: PRT
<213> ORGANISM: Human immunodeficiency virus type 1
<220> FEATURE:
<221> NAME/KEY: VARIANT
<222> LOCATION: (1)..(1)
<223> OTHER INFORMATION: X=I, L or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
```

-continued

<223> OTHER INFORMATION: X=F, I, L, V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y, M or W
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T

<400> SEQUENCE: 2

Xaa Xaa Xaa Xaa Xaa Xaa Xaa Xaa Xaa Xaa
1               5                   10

<210> SEQ ID NO 3
<211> LENGTH: 10
<212> TYPE: PRT
<213> ORGANISM: Human immunodeficiency virus type 1
<220> FEATURE:
<221> NAME/KEY: VARIANT
<222> LOCATION: (1)..(1)
<223> OTHER INFORMATION: X=I or V
<220> FEATURE:
<221> NAME/KEY: VARIANT
<222> LOCATION: (2)..(2)
<223> OTHER INFORMATION: X=T or S
<220> FEATURE:
<221> NAME/KEY: VARIANT
<222> LOCATION: (3)..(3)
<223> OTHER INFORMATION: X=F, W or Y
<220> FEATURE:
<221> NAME/KEY: VARIANT
<222> LOCATION: (4)..(4)
<223> OTHER INFORMATION: X=E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (7)..(7)
<223> OTHER INFORMATION: X=L, D or T
<220> FEATURE:
<221> NAME/KEY: VARIANT
<222> LOCATION: (8)..(8)
<223> OTHER INFORMATION: X=D, A or S
<220> FEATURE:
<221> NAME/KEY: VARIANT
<222> LOCATION: (9)..(9)
<223> OTHER INFORMATION: X=Y or F
<220> FEATURE:
<221> NAME/KEY: VARIANT
<222> LOCATION: (10)..(10)
<223> OTHER INFORMATION: X=Y or M

<400> SEQUENCE: 3

-continued

```
Xaa Xaa Xaa Xaa Xaa Leu Xaa Xaa Xaa Xaa
1               5                   10


<210> SEQ ID NO 4
<211> LENGTH: 11
<212> TYPE: PRT
<213> ORGANISM: Human immunodeficiency virus type 1
<220> FEATURE:
<221> NAME/KEY: VARIANT
<222> LOCATION: (1)..(1)
<223> OTHER INFORMATION: X=I, L or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L V, Y, M or W
<220> FEATURE:
<221> NAME/KEY: VARIANT
<222> LOCATION: (4)..(4)
<223> OTHER INFORMATION: X=D, E or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y M or W
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T
<220> FEATURE:
<221> NAME/KEY: VARIANT
<222> LOCATION: (11)..(11)
<223> OTHER INFORMATION: X=G, S, T, N, H, C, L, R, D, E, Q, M or K

<400> SEQUENCE: 4

Xaa Xaa Xaa Xaa Xaa Xaa Xaa Xaa Xaa Xaa Xaa
1               5                   10


<210> SEQ ID NO 5
<211> LENGTH: 12
<212> TYPE: PRT
<213> ORGANISM: Human immunodeficiency virus type 1
<220> FEATURE:
<221> NAME/KEY: VARIANT
<222> LOCATION: (1)..(1)
<223> OTHER INFORMATION: X=I, L, or V
<220> FEATURE:
<221> NAME/KEY: VARIANT
<222> LOCATION: (2)..(2)
<223> OTHER INFORMATION: X=T, S, A, V or C
<220> FEATURE:
<221> NAME/KEY: VARIANT
<222> LOCATION: (3)..(3)
<223> OTHER INFORMATION: X=F, I, L, V, Y, M or W
<220> FEATURE:
<221> NAME/KEY: VARIANT
<222> LOCATION: (4)..(4)
<223> OTHER INFORMATION: X=D, E or S
```

-continued

```
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, F, I, V, Y, M or W
<220> FEATURE:
<221> NAME/KEY: VARIANT
<222> LOCATION: (7)..(7)
<223> OTHER INFORMATION: X=L, D, T, F, I, V, Y, M or W
<220> FEATURE:
<221> NAME/KEY: VARIANT
<222> LOCATION: (8)..(8)
<223> OTHER INFORMATION: X=D, E, A or S
<220> FEATURE:
<221> NAME/KEY: VARIANT
<222> LOCATION: (9)..(9)
<223> OTHER INFORMATION: X=Y, F, I, L, V, M or W
<220> FEATURE:
<221> NAME/KEY: VARIANT
<222> LOCATION: (10)..(10)
<223> OTHER INFORMATION: X=Y, F, I, L, V, M or T
<220> FEATURE:
<221> NAME/KEY: VARIANT
<222> LOCATION: (11)..(11)
<223> OTHER INFORMATION: X=G, S, T, N, H, C, L, R, D, E, Q, M or K
<220> FEATURE:
<221> NAME/KEY: VARIANT
<222> LOCATION: (12)..(12)
<223> OTHER INFORMATION: X=P, M, R or K

<400> SEQUENCE: 5

Xaa Xaa Xaa Xaa Xaa Xaa Xaa Xaa Xaa Xaa Xaa Xaa
1               5                   10


<210> SEQ ID NO 6
<211> LENGTH: 12
<212> TYPE: PRT
<213> ORGANISM: Artificial Sequence
<220> FEATURE:
<223> OTHER INFORMATION: Stapled peptide NYAD-1
<220> FEATURE:
<221> NAME/KEY: MISC_FEATURE
<222> LOCATION: (4)..(4)
<223> OTHER INFORMATION: X=(S)-a-2-(4'-pentenyl)alanine
<220> FEATURE:
<221> NAME/KEY: MISC_FEATURE
<222> LOCATION: (8)..(8)
<223> OTHER INFORMATION: X=(S)-a-2-(4'-pentenyl)alanine

<400> SEQUENCE: 6

Ile Thr Phe Xaa Asp Leu Leu Xaa Tyr Tyr Gly Pro
1               5                   10


<210> SEQ ID NO 7
<211> LENGTH: 14
<212> TYPE: PRT
<213> ORGANISM: Artificial
<220> FEATURE:
<223> OTHER INFORMATION: Stapled peptide NYAD-13
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 7

Ile Thr Phe Xaa Asp Leu Leu Xaa Tyr Tyr Gly Lys Lys Lys
1               5                   10
```

<210> SEQ ID NO 8
<211> LENGTH: 15
<212> TYPE: PRT
<213> ORGANISM: Artificial Sequence
<220> FEATURE:
<223> OTHER INFORMATION: Stapled peptide NYAD-36
<220> FEATURE:
<221> NAME/KEY: MISC_FEATURE
<222> LOCATION: (4)..(4)
<223> OTHER INFORMATION: X=S-a-2-(7'-octenyl)alanine
<220> FEATURE:
<221> NAME/KEY: MISC_FEATURE
<222> LOCATION: (11)..(11)
<223> OTHER INFORMATION: X=S-a-2-(4'-pentenyl)alanine

<400> SEQUENCE: 8

```
Ile Ser Phe Xaa Glu Leu Leu Asp Tyr Tyr Xaa Glu Ser Gly Ser
1               5                   10                  15
```

<210> SEQ ID NO 9
<211> LENGTH: 14
<212> TYPE: PRT
<213> ORGANISM: Artificial Sequence
<220> FEATURE:
<223> OTHER INFORMATION: Stapled peptide NYAD-14
<220> FEATURE:
<221> NAME/KEY: MISC_FEATURE
<222> LOCATION: (8)..(8)
<223> OTHER INFORMATION: X=S-a-2-(4'-pentenyl)alanine
<220> FEATURE:
<221> NAME/KEY: MISC_FEATURE
<222> LOCATION: (12)..(12)
<223> OTHER INFORMATION: X=S-a-2-(4'-pentenyl)alanine

<400> SEQUENCE: 9

```
Ile Thr Phe Glu Asp Leu Leu Xaa Tyr Tyr Gly Xaa Lys Lys
1               5                   10
```

<210> SEQ ID NO 10
<211> LENGTH: 18
<212> TYPE: PRT
<213> ORGANISM: Artificial Sequence
<220> FEATURE:
<223> OTHER INFORMATION: Stapled peptide NYAD-203
<220> FEATURE:
<221> NAME/KEY: MISC_FEATURE
<222> LOCATION: (6)..(6)
<223> OTHER INFORMATION: X=S-a-2-(4'-pentenyl)alanine
<220> FEATURE:
<221> NAME/KEY: MISC_FEATURE
<222> LOCATION: (10)..(10)
<223> OTHER INFORMATION: X=S-a-2-(4'-pentenyl)alanine

<400> SEQUENCE: 10

```
Ala Gln Ala Val Lys Xaa Trp Met Thr Xaa Thr Leu Leu Val Ala Lys
1               5                   10                  15

Lys Lys
```

<210> SEQ ID NO 11
<211> LENGTH: 12
<212> TYPE: PRT
<213> ORGANISM: Artificial Sequence
<220> FEATURE:
<223> OTHER INFORMATION: Stapled peptide NYAD-15
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE -continued
<222> LOCATION: (8)..(8)
<223> OTHER INFORMATION: X=S-a-2-(4'-pentenyl)alanine

<400> SEQUENCE: 11

Ile Ser Phe Xaa Glu Leu Leu Xaa Tyr Tyr Gly Arg
1 5 10

<210> SEQ ID NO 12
<211> LENGTH: 13
<212> TYPE: PRT
<213> ORGANISM: Artificial Sequence
<220> FEATURE:
<223> OTHER INFORMATION: Stapled peptide NYAD-23
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 12

Ile Thr Phe Xaa Asp Ile Leu Xaa Tyr Tyr Gly Glu Lys
1 5 10

<210> SEQ ID NO 13
<211> LENGTH: 13
<212> TYPE: PRT
<213> ORGANISM: Artificial Sequence
<220> FEATURE:
<223> OTHER INFORMATION: Stapled peptide NYAD-24
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 13

Ile Ser Phe Xaa Glu Leu Leu Xaa Tyr Tyr Gly Glu Lys
1 5 10

<210> SEQ ID NO 14
<211> LENGTH: 12
<212> TYPE: PRT
<213> ORGANISM: Artificial Sequence
<220> FEATURE:
<223> OTHER INFORMATION: Stapled peptide NYAD-31
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 14

Ile Thr Phe Xaa Asp Trp Leu Xaa Tyr Tyr Gly Arg
1 5 10

<210> SEQ ID NO 15
<211> LENGTH: 12
<212> TYPE: PRT
<213> ORGANISM: Artificial Sequence
<220> FEATURE:
<223> OTHER INFORMATION: Stapled peptide NYAD-33
<220> FEATURE:

<221> NAME/KEY: MISC_FEATURE
<222> LOCATION: (4)..(4)
<223> OTHER INFORMATION: X=S-a-2-(7'-octenyl)alanine
<220> FEATURE:
<221> NAME/KEY: MISC_FEATURE
<222> LOCATION: (11)..(11)
<223> OTHER INFORMATION: X=S-a-2-(4'-pentenyl)alanine

<400> SEQUENCE: 15

Ile Ser Phe Xaa Glu Trp Leu Gln Tyr Tyr Xaa Arg
1 5 10

<210> SEQ ID NO 16
<211> LENGTH: 15
<212> TYPE: PRT
<213> ORGANISM: Artificial Sequence
<220> FEATURE:
<223> OTHER INFORMATION: Stapled peptide NYAD-24
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 16

Ile Ser Phe Xaa Glu Leu Leu Xaa Tyr Tyr Gly Arg Ser Gly Ser
1 5 10 15

<210> SEQ ID NO 17
<211> LENGTH: 15
<212> TYPE: PRT
<213> ORGANISM: Artificial Sequence
<220> FEATURE:
<223> OTHER INFORMATION: Stapled peptide NYAD-35
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 17

Ile Ser Phe Xaa Glu Leu Leu Xaa Tyr Tyr Gly Glu Ser Gly Ser
1 5 10 15

<210> SEQ ID NO 18
<211> LENGTH: 15
<212> TYPE: PRT
<213> ORGANISM: Artificial Sequence
<220> FEATURE:
<223> OTHER INFORMATION: Stapled peptide NYAD-37
<220> FEATURE:
<221> NAME/KEY: MISC_FEATURE
<222> LOCATION: (4)..(4)
<223> OTHER INFORMATION: X=S-a-2-(4'-pentenyl)alanine
<220> FEATURE:
<221> NAME/KEY: MISC_FEATURE
<222> LOCATION: (8)..(8)
<223> OTHER INFORMATION: X=S-a-2-(4'-pentenyl)alanine

<400> SEQUENCE: 18

Ile Ser Phe Xaa Glu Ile Leu Xaa Tyr Tyr Gly Glu Ser Gly Ser
1 5 10 15

<210> SEQ ID NO 19
<211> LENGTH: 15

-continued

<212> TYPE: PRT
<213> ORGANISM: Artificial Sequence
<220> FEATURE:
<223> OTHER INFORMATION: Linear peptide NYAD-40

<400> SEQUENCE: 19

Ile Ser Phe Asp Glu Leu Leu Asp Tyr Tyr Gly Glu Ser Gly Ser
1 5 10 15

<210> SEQ ID NO 20
<211> LENGTH: 15
<212> TYPE: PRT
<213> ORGANISM: Artificial Sequence
<220> FEATURE:
<223> OTHER INFORMATION: Linear peptide NYAD-41

<400> SEQUENCE: 20

Ile Ser Phe Asp Glu Leu Leu Asp Tyr Tyr Gly Glu Ser Gly Ser
1 5 10 15

<210> SEQ ID NO 21
<211> LENGTH: 10
<212> TYPE: PRT
<213> ORGANISM: Human immunodeficiency virus
<220> FEATURE:
<221> NAME/KEY: VARIANT
<222> LOCATION: (2)..(2)
<223> OTHER INFORMATION: X=T or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, I or W
<220> FEATURE:
<221> NAME/KEY: VARIANT
<222> LOCATION: (8)..(8)
<223> OTHER INFORMATION: X=D or Q

<400> SEQUENCE: 21

Ile Xaa Phe Glu Xaa Xaa Leu Xaa Tyr Tyr
1 5 10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: X=T or S
<220> FEATURE:
<221> NAME/KEY: VARIANT
<222> LOCATION: (5)..(5)
<220> FEATURE:
<221> NAME/KEY: VARIANT
<222> LOCATION: (6)..(6)
<220> FEATURE:
<221> NAME/KEY: VARIANT
<222> LOCATION: (8)..(8)

<400> SEQUENCE: 22

Ile Xaa Phe Glu Xaa Xaa Leu Xaa Tyr Tyr Gly
1 5 10

<210> SEQ ID NO 23
<211> LENGTH: 12

```
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: X=T or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, I or W
<220> FEATURE:
<221> NAME/KEY: VARIANT
<222> LOCATION: (8)..(8)
<223> OTHER INFORMATION: X=D or Q
<220> FEATURE:
<221> NAME/KEY: VARIANT
<222> LOCATION: (12)..(12)
<223> OTHER INFORMATION: X=K, E or R

<400> SEQUENCE: 23

Ile Xaa Phe Glu Xaa Xaa Leu Xaa Tyr Tyr Gly Xaa
1               5                   10


<210> SEQ ID NO 24
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: X=T or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, I or W
<220> FEATURE:
<221> NAME/KEY: VARIANT
<222> LOCATION: (8)..(8)
<223> OTHER INFORMATION: X=D or Q
<220> FEATURE:
<221> NAME/KEY: VARIANT
<222> LOCATION: (12)..(12)
<223> OTHER INFORMATION: X=K, E or R
<220> FEATURE:
<221> NAME/KEY: VARIANT
<222> LOCATION: (13)..(13)
<223> OTHER INFORMATION: X=K or S

<400> SEQUENCE: 24

Ile Xaa Phe Glu Xaa Xaa Leu Xaa Tyr Tyr Gly Xaa Xaa
1               5                   10


<210> SEQ ID NO 25
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: X=T or S
<220> FEATURE:
```

-continued

```
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, I or W
<220> FEATURE:
<221> NAME/KEY: VARIANT
<222> LOCATION: (8)..(8)
<223> OTHER INFORMATION: X=D or Q
<220> FEATURE:
<221> NAME/KEY: VARIANT
<222> LOCATION: (12)..(12)
<223> OTHER INFORMATION: X=K, E or R
<220> FEATURE:
<221> NAME/KEY: VARIANT
<222> LOCATION: (13)..(13)
<223> OTHER INFORMATION: X=K or S
<220> FEATURE:
<221> NAME/KEY: VARIANT
<222> LOCATION: (14)..(14)
<223> OTHER INFORMATION: X=K or G

<400> SEQUENCE: 25

Ile Xaa Phe Glu Xaa Xaa Leu Xaa Tyr Tyr Gly Xaa Xaa Xaa
1               5                   10


<210> SEQ ID NO 26
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: X=T or S
<220> FEATURE:
<221> NAME/KEY: VARIANT
<222> LOCATION: (5)..(5)
<223> OTHER INFORMATION: X=D or E
<220> FEATURE:
<221> NAME/KEY: VARIANT
<222> LOCATION: (6)..(6)
<223> OTHER INFORMATION: X=L, I or W
<220> FEATURE:
<221> NAME/KEY: VARIANT
<222> LOCATION: (8)..(8)
<223> OTHER INFORMATION: X=D or Q
<220> FEATURE:
<221> NAME/KEY: VARIANT
<222> LOCATION: (12)..(12)
<223> OTHER INFORMATION: X=K, E or R
<220> FEATURE:
<221> NAME/KEY: VARIANT
<222> LOCATION: (13)..(13)
<223> OTHER INFORMATION: X=K or S
<220> FEATURE:
<221> NAME/KEY: VARIANT
<222> LOCATION: (14)..(14)
<223> OTHER INFORMATION: X=K or G

<400> SEQUENCE: 26

Ile Xaa Phe Glu Xaa Xaa Leu Xaa Tyr Tyr Gly Xaa Xaa Xaa Ser
1               5                   10                  15
```